(12) United States Patent
Gunderson

(10) Patent No.: US 10,335,047 B2
(45) Date of Patent: Jul. 2, 2019

(54) AUTOMATIC HEART RATE DIAGNOSTICS

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/603,901

(22) Filed: May 24, 2017

(65) Prior Publication Data
US 2018/0035899 A1 Feb. 8, 2018

Related U.S. Application Data

(60) Provisional application No. 62/370,156, filed on Aug. 2, 2016.

(51) Int. Cl.
*A61B 5/00* (2006.01)
*A61B 5/04* (2006.01)
(Continued)

(52) U.S. Cl.
CPC ........ *A61B 5/0245* (2013.01); *A61B 5/02455* (2013.01); *A61B 5/042* (2013.01);
(Continued)

(58) Field of Classification Search
CPC .... A61N 1/3956; A61N 1/3925; A61B 5/042; A61B 5/746; A61B 5/0245;
(Continued)

(56) References Cited

U.S. PATENT DOCUMENTS 5,117,824 A   6/1992 Keimel et al.
5,545,186 A   8/1996 Olson et al.
(Continued)

FOREIGN PATENT DOCUMENTS

WO   2002067449 A2   8/2002
WO   2007033194 A2   3/2007

OTHER PUBLICATIONS

Giuberti et al., "Automatic UPDRS Evaluation in the Sit-to-Stand Task of Parkinsonians: Kinetic Analysis and Comparative Outlook on the Leg Agility Task", IEEE Journal of Biomedical and Health Informatics, May 2015, pp. 2168-2194, vol. 19, No. 3.
(Continued)

*Primary Examiner* — Catherine M Voorhees

(57) ABSTRACT

In some examples, processing circuitry of a medical device system determines, for each of a plurality of periods, a plurality of heart rates of a patient based on a cardiac electrogram signal, and identifies a first subset of the plurality of heart rates as nighttime heart rates and a second subset of the plurality of heart rates as resting heart rates. The processing circuitry determines a representative nighttime heart rate based on the first subset of the plurality of heart rates, determines a representative resting heart rate based on the second subset of the plurality of heart rates, and determines a nocturnal dip base on the representative nighttime heart rate and the representative resting heart rate. The processing circuitry compares at least one of the representative nighttime heart rate, the representative resting heart rate, and the nocturnal dip in heart rate to a respective threshold value, and determines whether to generate an alert indicating a change in the cardiac function of the patient based on the comparison.

20 Claims, 17 Drawing Sheets

(51) Int. Cl.
*A61B 5/11* (2006.01)
*A61N 1/39* (2006.01)
*A61B 5/042* (2006.01)
*A61B 5/0245* (2006.01)

(52) U.S. Cl.
CPC ........ *A61B 5/04012* (2013.01); *A61B 5/1116* (2013.01); *A61B 5/7246* (2013.01); *A61B 5/746* (2013.01); *A61N 1/3925* (2013.01); *A61N 1/3956* (2013.01)

(58) Field of Classification Search
CPC . A61B 5/1116; A61B 5/02455; A61B 5/7246; A61B 5/04012
See application file for complete search history.

(56) References Cited

U.S. PATENT DOCUMENTS

| | | | |
|---|---|---|---|
| 5,755,736 | A | 5/1998 | Gillberg et al. |
| 7,141,026 | B2 | 11/2006 | Aminian et al. |
| 8,744,572 | B1 | 6/2014 | Greenhut et al. |
| 2006/0030892 | A1 | 2/2006 | Kadhiresan et al. |
| 2006/0276848 | A1* | 12/2006 | Min .................. A61B 5/0535 607/17 |
| 2007/0067005 | A1 | 3/2007 | Schatz et al. |
| 2008/0255626 | A1 | 10/2008 | Fricke et al. |
| 2008/0281550 | A1 | 11/2008 | Hogle et al. |
| 2009/0312649 | A1* | 12/2009 | Lian .................. A61B 5/0538 600/484 |
| 2010/0010361 | A1 | 1/2010 | Boute et al. |
| 2010/0030090 | A1 | 2/2010 | Zhang et al. |
| 2010/0030292 | A1 | 2/2010 | Sarkar et al. |
| 2010/0087745 | A1 | 4/2010 | Fischell et al. |
| 2011/0040572 | A1 | 2/2011 | Chmiel et al. |
| 2011/0077865 | A1 | 3/2011 | Chen et al. |
| 2011/0082350 | A1 | 4/2011 | Koh |
| 2011/0148400 | A1* | 6/2011 | Doerr .................. A61B 5/103 324/207.11 |
| 2013/0079861 | A1 | 3/2013 | Reinert et al. |
| 2013/0085677 | A1 | 4/2013 | Modi et al. |
| 2013/0123684 | A1 | 5/2013 | Giuffrida et al. |
| 2014/0276928 | A1 | 9/2014 | Vanderpool et al. |
| 2014/0330172 | A1 | 11/2014 | Jovanov et al. |
| 2014/0364769 | A1 | 12/2014 | Chang et al. |
| 2015/0342540 | A1 | 12/2015 | An et al. |
| 2016/0038093 | A1* | 2/2016 | Sharma .................. A61B 5/7435 600/481 |
| 2016/0155313 | A1 | 6/2016 | Chang et al. |
| 2016/0209232 | A1 | 7/2016 | Yang et al. |

OTHER PUBLICATIONS

Veltink, et al., "Detection of Static and Dynamic Activities Using Uniaxial Accelerometers", IEEE Transacations on Rehabilitation Engineering, Dec. 1996, pp. 1063-6528, vol. 4, No. 4.

Wieling et al., "Testing for Autonomic Neuropathy: Heart Rate Changes After Orthostatic Manoeuvers and Static Muscle Contractions," Clinical Science (London), 1983, pp. 581-586, vol. 64, No. 6.

(PCT/US2017/041451) PCT Notification of Transmittal of the International Search Report and the Written Opinion of the International Searching Authority, or the Declaration, dated Sep. 21, 2017, 14 pages.

(PCT/US2017/041483) PCT Notification of Transmittal of the International Search Report and the Written Opinion of the International Searching Authority, or the Declaration, dated Sep. 25, 2017, 14 pages.

(PCT/US2017/041713) PCT Notification of Transmittal of the International Search Report and the Written Opinion of the International Searching Authority, or the Declaration, dated Sep. 27, 2017, 14 pages.

(PCT/US2017/041701) PCT Notification of Transmittal of the International Search Report and the Written Opinion of the International Searching Authority, or the Declaration, dated Oct. 18, 2017, 14 pages.

(PCT/US2017/041621) PCT Notification of Transmittal of the International Search Report and the Written Opinion of the International Searching Authority, or the Declaration, dated Oct. 27, 2017, 14 pages.

* cited by examiner

AUTOMATIC HEART RATE DIAGNOSTICS

RELATED APPLICATIONS

This application claims the benefit of U.S. Provisional Application No. 62/370,156, filed Aug. 2, 2016, incorporated by reference herein.

FIELD

The disclosure relates generally to medical device systems and, more particularly, medical device systems configured to monitor patient parameters.

BACKGROUND

Implantable medical devices (IMDs) and external, e.g., wearable, medical devices, including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events and, in some cases, respond to the episodes as needed with pacing therapy or high-voltage anti-tachyarrhythmia shocks, e.g., cardioversion or defibrillation shocks. Some IMDs include, or are or part of a system that includes, sensors that generate other physiological signals, such as signals that vary based on patient movement or activity, cardiovascular pressure, blood oxygen saturation, edema, or thoracic impedance. Physiological parameters determined based on such signals may be used to assist in the detection of arrhythmia, as well as the detection or monitoring of other cardiac conditions, such as heart failure or infarction, or, more generally, cardiac health.

SUMMARY

In general, this disclosure is directed to techniques for automatically detecting and monitoring objective measures of cardiac function. A number of such techniques may include determining a respective value for each of a plurality of parameters of a patient's heart rate, e.g., a representative resting heart rate, a representative nighttime heart rate, and a nocturnal dip in heart rate, during each of a plurality of periods, which may be approximately one day. In particular, the magnitude of a nocturnal dip in a patient's heart rate may provide an objective measure of cardiac health. A low magnitude of nocturnal dip in a patient's heart rate, or an abrupt decrease in the magnitude of a nocturnal dip, have been shown to predict patient mortality. Thus, it is desirable to track trends in the parameters of a patient's heart rate over time by automatically detecting the patient's heart rate and calculating values for parameters such as representative resting heart rate, representative nighttime heart rate, and nocturnal dip in heart rate therefrom.

In one example, a medical device system comprises sensing circuitry configured to sense a cardiac electrogram signal of a patient via a plurality of electrodes and generate a signal that varies as a function of movement and posture of the patient; and processing circuitry configured to, for each of a plurality of periods, determine a plurality of heart rates of the patient based on the cardiac electrogram signal. The processing circuitry also is configured to identify a first subset of the plurality of heart rates as nighttime heart rates, identify a second subset of the plurality of heart rates as resting heart rates, determine a representative nighttime heart rate based on the first subset of the plurality of heart rates, determine a representative resting heart rate based on the second subset of the plurality of heart rates, determine a nocturnal dip based on the representative nighttime heart rate and the representative resting heart rate, and compare at least one of the representative nighttime heart rate, the representative resting heart rate, and the nocturnal dip to a respective threshold value. The processing circuitry may also be configured to determine whether to generate an alert indicating a change in the cardiac function of the patient based on the comparison.

In another example, a method comprises generating, by sensing circuitry configured to sense a cardiac electrogram signal of a patient via a plurality of electrodes, a signal that varies as a function of movement and posture of the patient, and, for each of a plurality of periods, determining, by processing circuitry, a plurality of heart rates of the patient based on the cardiac electrogram signal. In some examples, the method may further comprise identifying a first subset of the plurality of heart rates as nighttime heart rates, identifying a second subset of the plurality of heart rates as resting heart rates, determining a representative nighttime heart rate based on the first subset of the plurality of heart rates, determining a representative resting heart rate based on the second subset of the plurality of heart rates, determining a nocturnal dip based on the representative nighttime heart rate and the representative resting heart rate, and comparing at least one of the representative nighttime heart rate, the representative resting heart rate, and the nocturnal dip to a respective threshold value. The method may further include determining whether to generate an alert indicating a change in the cardiac function of the patient based on the comparison.

In other examples, a medical device system comprises means for performing any of the methods or techniques described herein.

In other examples, non-transitory computer-readable media comprise program instructions that, when executed by processing circuitry of a medical device system, cause the medical device system to perform any of the methods or techniques described herein.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

In general, this disclosure describes example techniques related to automatically determining whether a change in a patient's cardiac function has occurred, based on one or more parameters of the patient's heart rate including a representative resting heart rate, a representative nighttime heart rate, and a nocturnal dip in heart rate, and providing an alert indicating that a change in cardiac function has occurred. It is further contemplated that, in some example techniques, one or more parameters of a cardiac therapy may be modified based on a determination that a change in the patient's cardiac function has occurred. In the following description, references are made to illustrative examples. It is understood that other examples may be utilized without departing from the scope of the disclosure.

Figure 1:
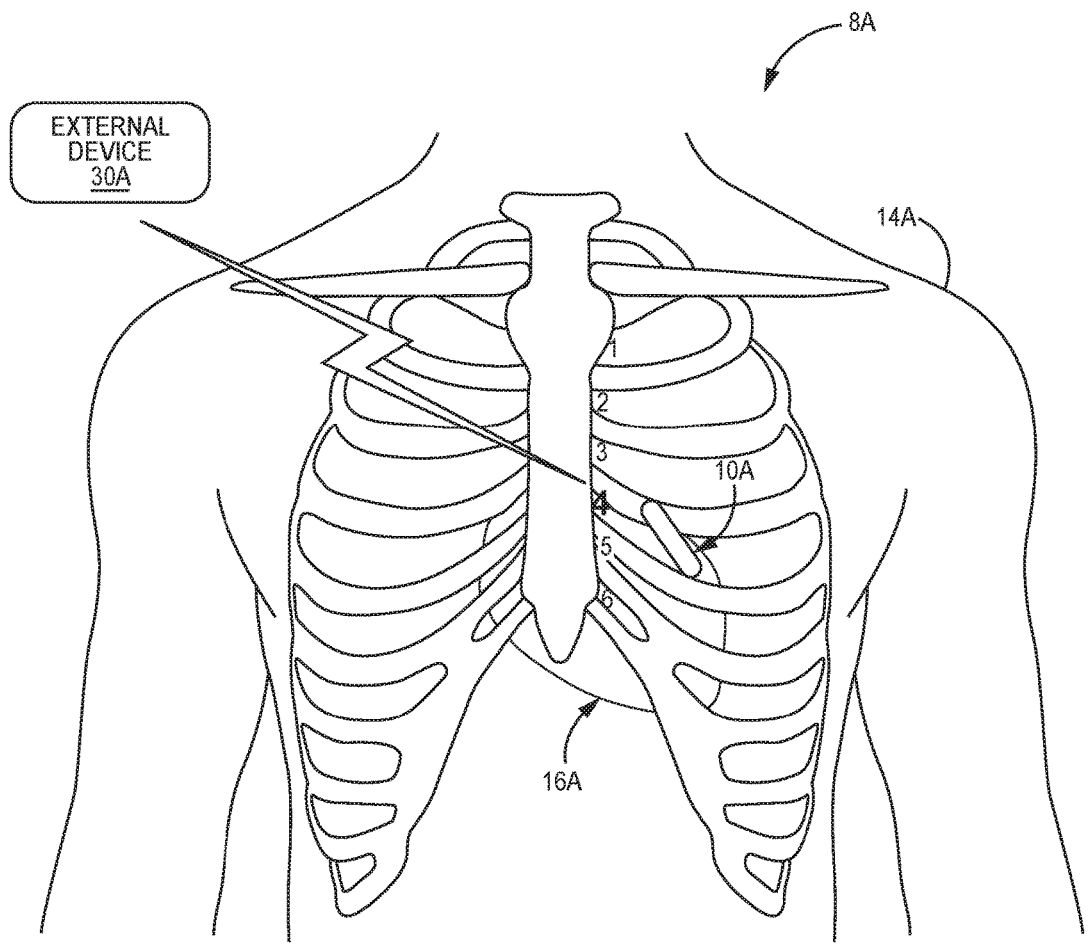
FIG. 1 is a conceptual drawing illustrating an example configuration of an implantable cardiac monitor in conjunction with a patient.

FIG. 1 is a conceptual drawing illustrating an example medical device system 8A in conjunction with a patient 14A.

Medical device system 8A is an example of a medical device system configured to implement the techniques described herein for determining whether a change in the cardiac function of a patient has occurred, and generating an alert notifying a user or clinician of the change in cardiac function. In the illustrated example, medical device system 8A includes an IMD 10A and an external device 30A.

IMD 10A is an insertable cardiac monitor (ICM) capable of sensing and recording cardiac EGM signals from a position outside of heart 16A, and will be referred to as ICM 10A hereafter. In some examples, ICM 10A includes or is coupled to one or more additional sensors that generate one or more other physiological signals, such as signals that vary based on patient motion and/or posture, blood flow, or respiration. ICM 10A may be implanted outside of the thorax of patient 14A, e.g., subcutaneously or submuscularly, such as the pectoral location illustrated in FIG. 2. In some examples, ICM 10A may take the form of a Reveal LINQ™ ICM, available from Medtronic plc, of Dublin, Ireland.

External device 30A may be used to program commands or operating parameters into ICM 10A for controlling its functioning, e.g., when configured as a programmer for ICM 10A. External device 30A may be used to interrogate ICM 10A to retrieve data, including device operational data as well as physiological data accumulated in IMD memory. The accumulated physiological data may include heart rates generally, and periodically determined nighttime heart rates, resting heart rates and nocturnal dips (including means, medians, and/or trends thereof) determined by ICM 10A. The interrogation may be automatic, e.g., according to a schedule, or in response to a remote or local user command. Programmers, external monitors, and consumer devices are examples of external devices 30A that may be used to interrogate ICM 10A. Examples of communication techniques used by ICM 10A and external device 30A include radiofrequency (RF) telemetry, which may be an RF link established via Bluetooth, WiFi, or medical implant communication service (MICS).

Both ICM 10A and external device 30A include processing circuitry, and the processing circuitry of either or both devices may perform the techniques described herein, such as determining a plurality of patient heart rates for a period, determining a representative nighttime heart rate and a representative resting heart rate, determine a nocturnal dip based on the representative nighttime heart rate and the representative resting heart rate, and compare at least one of the representative nighttime heart rate, representative resting heart rate, and the nocturnal dip to a respective threshold value.

Based on the comparison, the processing circuitry may also be configured to provide an alert to a user, e.g., clinician or patient 14A, that a change in the cardiac function of the patient has occurred, e.g., via external device 30B. Although ICM 10A is not described as being configured to deliver therapy, patient 14A, a clinician, or another implanted or external medical device may deliver therapy or change the parameters of a therapy to be delivered based on the change in the patient's cardiac function indicated by medical device system 8A. In examples in which therapy may be delivered to the patient, the therapy may be configured to treat and/or prevent cardiac events or maladies, such as ventricular tachyarrhythmia, heart failure, and myocardial infarction.

Although not illustrated in the example of FIG. 1, a medical device system configured to implement the techniques of this disclosure may include one or more implanted or external medical devices in addition to or instead of ICM 10A. For example, a medical device system may include a pressure sensing IMD 50, vascular ICD (e.g., ICD 10B of FIG. 3), extravascular ICD (e.g., ICD 10C of FIGS. 4A-5), or cardiac pacemaker (e.g., IPD 10D of FIGS. 4A-6 or a cardiac pacemaker implanted outside the heart but coupled to intracardiac or epicardial leads). One or more such devices may sense physiological signals of the patient, such as a cardiac electrogram signal, and include processing circuitry configured to perform, in whole or in part, the techniques described herein for determining whether a change in the cardiac function of the patient has occurred. The implanted devices may communicate with each other and/or an external device 30, and one of the implanted or external devices may ultimately determine whether a change in the cardiac function of the patient has occurred based on information received from the other device(s).

Medical device system 8A is one example of a medical device system that may be configured to implement the techniques described herein for determining whether a change in the cardiac function of a patient has occurred. Other example medical device systems that may be configured to implement the techniques are described with respect to FIGS. 2-6. Although described herein primarily in the context of implantable medical devices generating physiological signals and, in some examples, delivering therapy, a medical device system that implements the techniques described in this disclosure may additionally or alternatively include an external medical device, e.g., external cardiac monitor, and/or external pacemaker, cardioverter and/or defibrillator, configured to generate one or more of the physiological signals described herein, determine whether a change in the cardiac function of a patient has occurred, provide an alert, and/or deliver one or more of the preventative therapies described herein.

Figure 2:
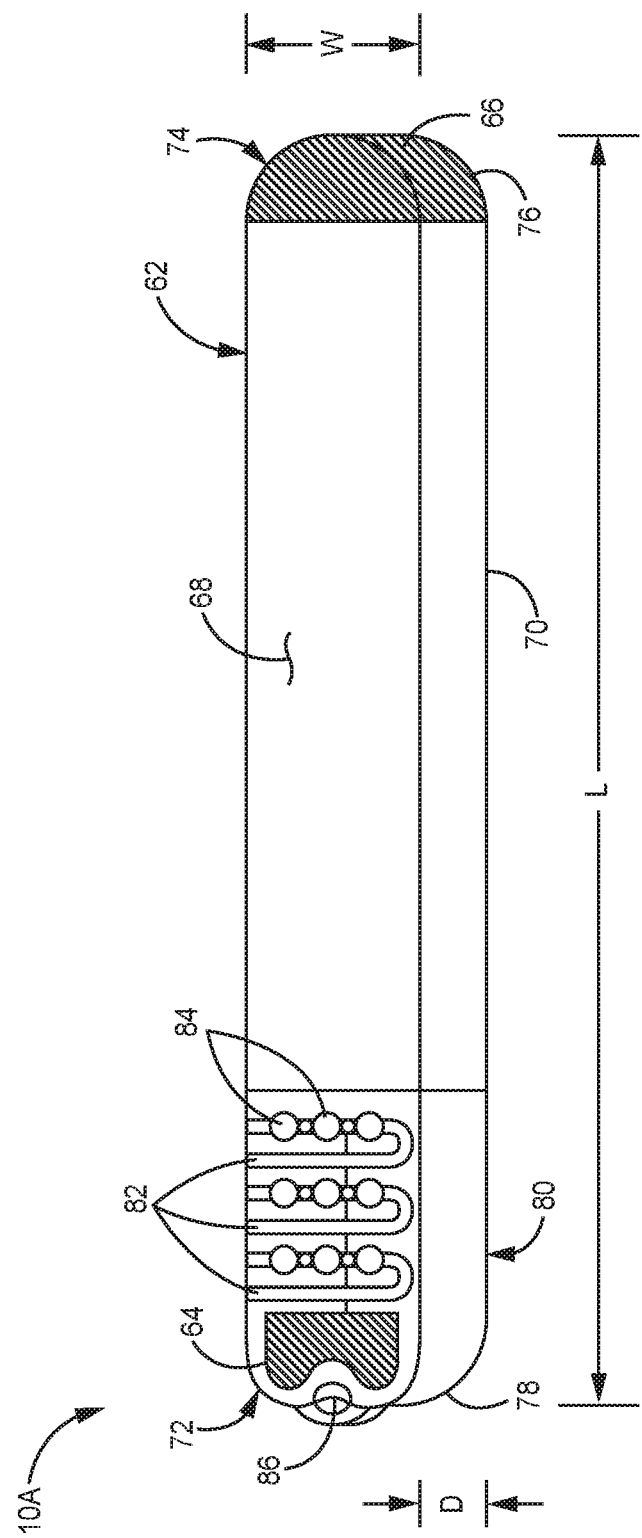
FIG. 2 is a perspective drawing illustrating an example configuration of the implantable cardiac monitor of FIG. 1.

FIG. 2 is a conceptual drawing illustrating an example configuration of ICM 10A. In the example shown in FIG. 2, ICM 10A may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10A and protects the circuitry contained therein from body fluids. Electrical feedthroughs provide electrical connection of electrodes 64 and 66.

In the example shown in FIG. 2, ICM 10A is defined by a length L, a width W and thickness or depth D and is in the form of an elongated rectangular prism wherein the length L is much larger than the width W which in turn is larger than the depth D. In one example, the geometry of the ICM 10A—in particular a width W greater than the depth D—is selected to allow ICM 10B to be inserted under the skin of the patient using a minimally invasive procedure and to remain in the desired orientation during insertion. For example, the device shown in FIG. 2 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10A may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10A may range from 2 mm to 9 mm. In other examples, the depth D of ICM 10B may range from 2 mm to 5 mm and may be any single or range of depths from 2 mm to 9 mm. In addition, ICM 10A according to an example of the present disclosure is has a geometry and size designed for ease of implant and patient comfort. Examples of ICM 10A described in this disclosure may have a volume of three cubic centimeters (cm) or less, 1.5 cubic cm or less or any volume between three and 1.5 cubic centimeters.

In the example shown in FIG. 2, once inserted within the patient, the first major surface 68 faces outward, toward the skin of the patient while the second major surface 70 is located opposite the first major surface 68. In addition, in the example shown in FIG. 2, proximal end 72 and distal end 74 are rounded to reduce discomfort and irritation to surrounding tissue once inserted under the skin of the patient. ICM 10A, including instrument and method for inserting ICM 10A is described, for example, in U.S. Patent Publication No. 2014/0276928, incorporated herein by reference in its entirety.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 82 to another medical device, which may be another implantable device or an external device, such as external device 30A. In some example, electrodes 64 and 66 may additionally or alternatively be used for sensing any biopotential signal of interest, which may be, for example, an EGM, EEG, EMG, or a nerve signal, from any implanted location.

In the example shown in FIG. 2, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 2, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 2, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10A may include electrodes on both major surface 68 and 70 at or near the proximal and distal ends of the device, such that a total of four electrodes are included on ICM 10A. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 2, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10A to transmit and/or receive data. In other examples, integrated antenna 82 may be formed on the opposite major surface as proximal electrode 64, or may be incorporated within the housing 82 of ICM 10A. In the example shown in FIG. 2, anti-migration projections 84 are located adjacent to integrated antenna 82 and protrude away from first major surface 68 to prevent longitudinal movement of the device. In the example shown in FIG. 2, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 2 header assembly 80 includes suture hole 86, which provides another means of securing ICM 10A to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10A.

Figure 3:
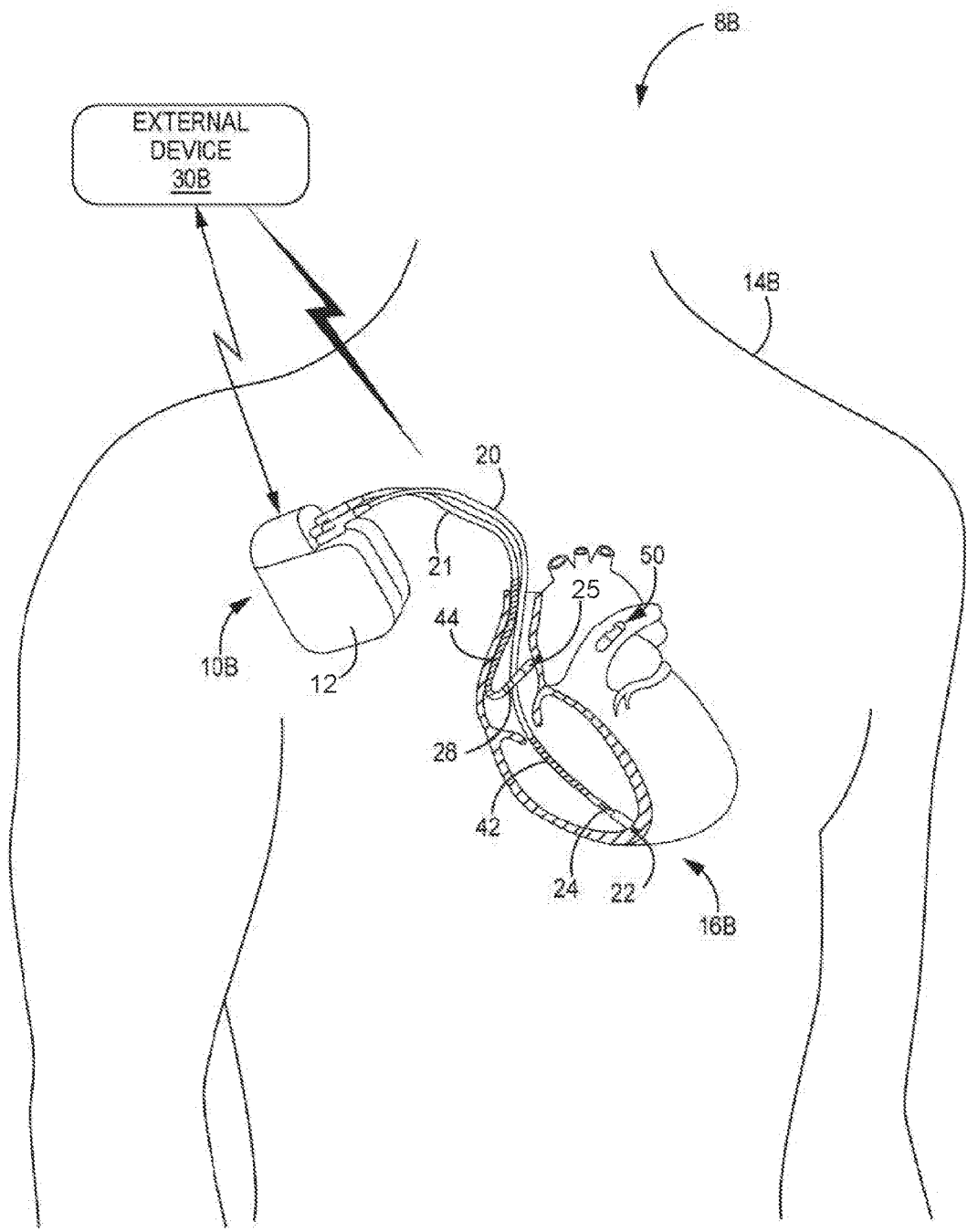
FIG. 3 is a conceptual drawing illustrating another example medical device system in conjunction with a patient.

FIG. 3 is a conceptual drawing illustrating another example medical device system 8B in conjunction with a patient 14B. Medical device system 8B is another example of a medical device system configured to implement the techniques described herein for determining whether a change in a patient's cardiac function has occurred. In the illustrated example, medical device system 8A includes an implantable medical device (IMD) 10B coupled to a ventricular lead 20 and an atrial lead 21. IMD 10B is an implantable cardioverter-defibrillator (ICD) capable of delivering pacing, cardioversion and defibrillation therapy to the heart 16B of a patient 14B, and will be referred to as ICD 10B hereafter.

Ventricular lead 20 and atrial lead 21 are electrically coupled to ICD 10B and extend into the patient's heart 16B. Ventricular lead 20 includes electrodes 22 and 24 shown positioned on the lead in the patient's right ventricle (RV) for sensing ventricular EGM signals and pacing in the RV. Atrial lead 21 includes electrodes 25 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 3.

ICD 10B may use both ventricular lead 20 and atrial lead 21 to acquire cardiac electrogram (EGM) signals from patient 14B and to deliver therapy in response to the acquired data. Medical device system 8B is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10B may transmit EGM signal data and cardiac rhythm episode data acquired by ICD 10B, as well as data regarding delivery of therapy by ICD 10B, to an external device 30B. External device 30A may be a computing device, e.g., used in a home, ambulatory, clinic, or hospital setting, to communicate with ICD 10A via wireless telemetry. External device 30A may be coupled to a remote patient monitoring system, such as Carelink®, available from Medtronic plc, of Dublin, Ireland. External device 30A may be, as examples, a programmer, external monitor, or consumer device, e.g., a smart phone.

External device 30B may be used to program commands or operating parameters into ICD 10B for controlling its functioning, e.g., when configured as a programmer for ICD 10B. External device 30B may be used to interrogate ICD 10B to retrieve data, including device operational data as well as physiological data accumulated in IMD memory, such as data associated with a heart rate parameter of a patient. The interrogation may be automatic, e.g., according to a schedule, or in response to a remote or local user command. Programmers, external monitors, and consumer devices are examples of external devices 30A that may be used to interrogate ICD 10B. Examples of communication techniques used by ICD 10B and external device 30B include radiofrequency (RF) telemetry, which may be an RF link established via Bluetooth, WiFi, or medical implant communication service (MICS).

Medical device system 8B is an example of a medical device system configured to determine whether a change in a patient's cardiac function has occurred, responsively provide an alert indicating that the change in cardiac function has occurred, and/or cause another implanted or external medical device to deliver therapy or change the parameters of a therapy to be delivered based on the change in the patient's cardiac function. The techniques may be performed by processing circuitry of medical device system 8B, such as processing circuitry of one or both of ICD 10B and external device 30B, individually, or collectively.

The techniques include determining a respective value for each of a plurality of heart rates of a patient, e.g., a representative nighttime heart rate, a representative resting heart rate, and a nocturnal dip, during each of a plurality of periods, which may be at least one hour, such as between approximately one day and approximately three days, e.g., in one example, approximately one day. In some examples, the processing circuitry of medical device system 8B indicates that a change in the cardiac function of the patient has occurred if the value of the representative resting heart rate is equal to or greater than a threshold value for any given period. In another example, the processing circuitry of medical device system 8B indicates that a change in the cardiac function of the patient has occurred if the value of the nocturnal dip is equal to or less than a threshold value for any given period. In still other examples, the processing circuitry of medical device system 8B indicates that a change in the cardiac function of the patient has occurred if the value for the nocturnal dip is equal to or greater than a threshold value, wherein the threshold value comprises the number of times that the nocturnal dip was equal to or less than a predetermined percentage value during one or more previous periods.

Figure 4A:
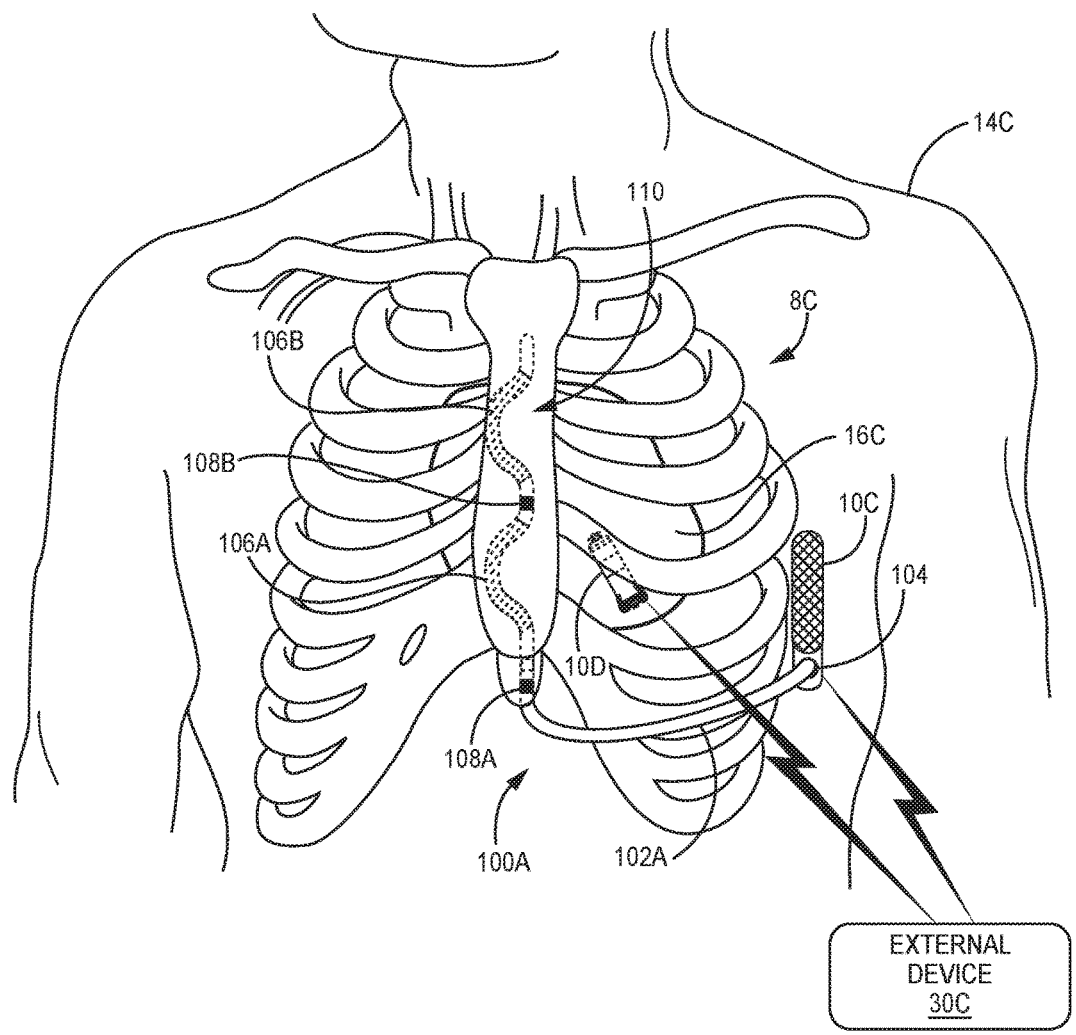
FIGS. 4A-4C are front-view, side-view, and top-view conceptual drawings, respectively, illustrating another example medical device system in conjunction with a patient.
Figure 4B:
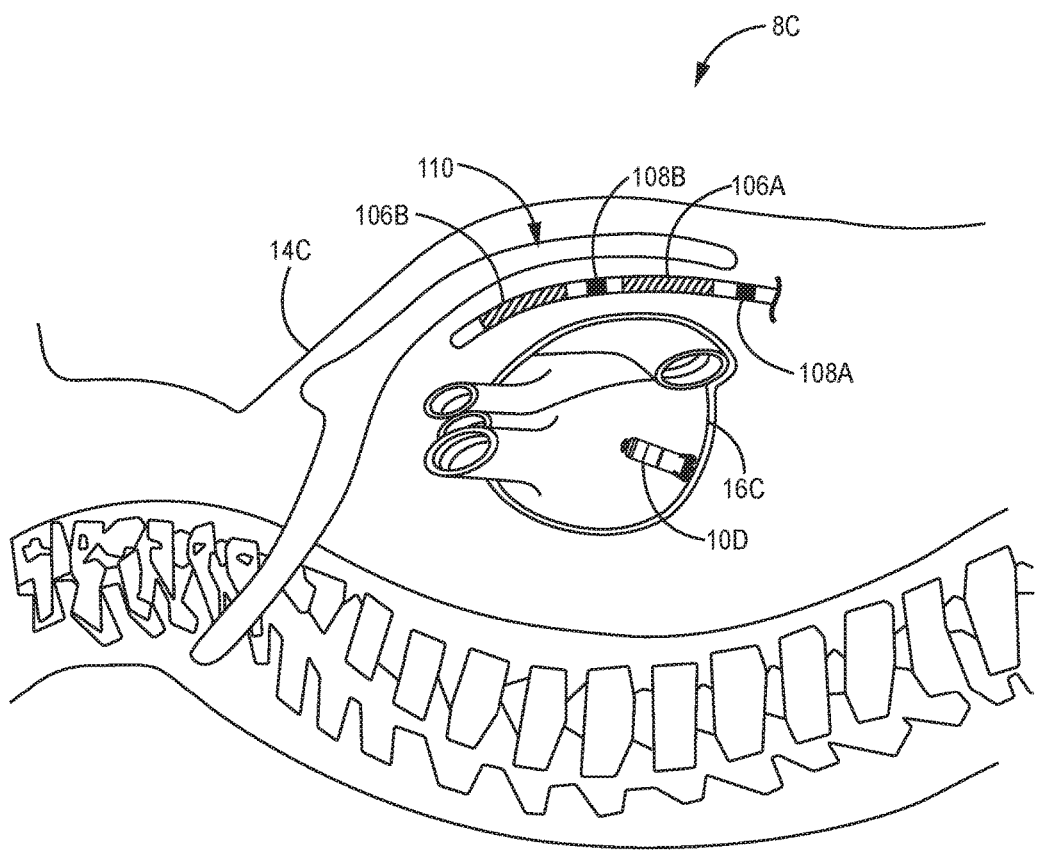
Figure 4C:
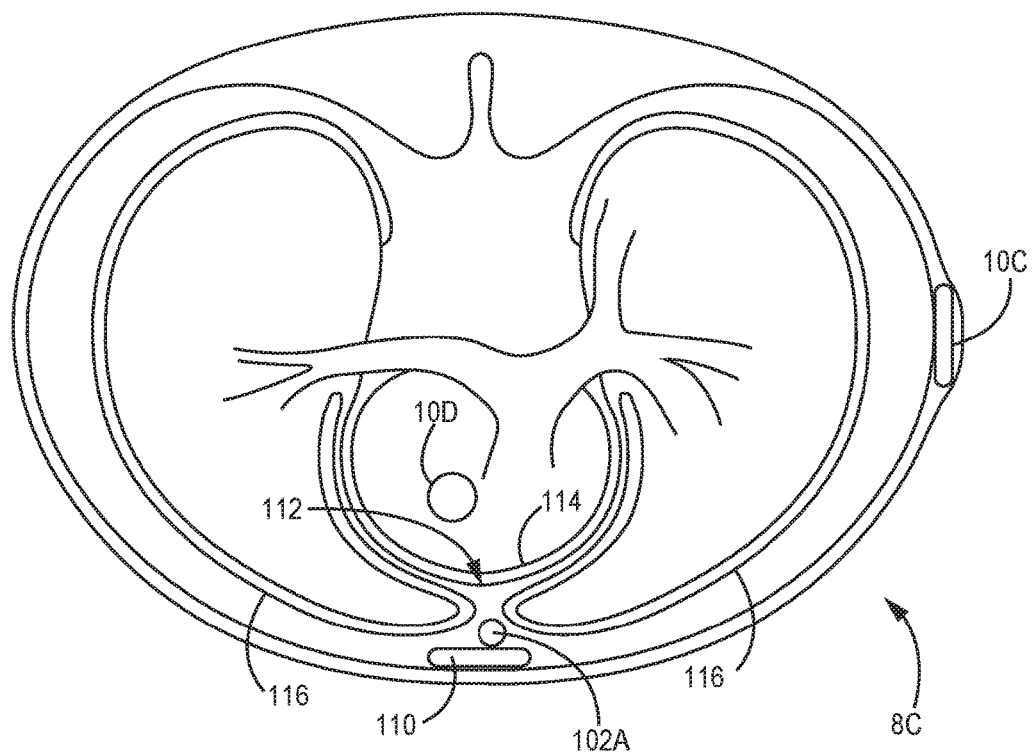

FIGS. 4A-4C are front-view, side-view, and top-view conceptual drawings, respectively, illustrating another example medical device system 8C in conjunction with a patient 14C. Medical device system 8C is another example of a medical device system configured to implement the techniques described herein for determining whether a change in the cardiac function of a patient has occurred, and, in some examples, causing another implanted or external medical device may deliver therapy or change the parameters of a therapy to be delivered based on the change in the patient's cardiac function indicated by medical device system 8C.

In the illustrated example, medical device system 8C includes an extracardiovascular ICD system 100A implanted within a patient 14C. ICD system 100A includes an IMD 10C, which is an ICD and is referred to hereafter as ICD 10C, connected to at least one implantable cardiac defibrillation lead 102A. ICD 10C is configured to deliver high-energy cardioversion or defibrillation pulses to a patient's heart 16C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracic and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between defibrillation electrodes 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the defibrillation electrode sections 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s) 108"), located along the distal portion of defibrillation lead 102A. In the example illustrated in FIG. 4A and FIG. 4B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the defibrillation electrode sections 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable of sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10D and ICD 10C is described in commonly-assigned U.S. patent application Ser. No. 13/756,085, titled, "SYSTEMS AND METHODS FOR LEADLESS PACING AND SHOCK THERAPY," filed Jan. 31, 2013, the entire content of which is incorporated by reference herein.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 21 may allow a user to program any coefficients, weighting factors, or techniques for determining difference metrics, scores, and/or thresholds, or other data described herein as being used by a medical device system to determine whether an acute cardiac event is predicted.

Although FIGS. 4A-4C are shown or described in the context of IPD 10D and extracardiovascular ICD system 100A that includes lead 102A with a substernally placed distal portion, techniques in accordance with one or more aspects of the present disclosure may be applicable to other coexistent systems. For example, an extracardiovascular ICD system may include a lead having a distal portion that is implanted subcutaneously above the sternum (or other location) instead of being implanted substernally. As another example, instead of an IPD, a pacing system may be implanted having a pacemaker and one or more leads connected to and extending from the pacemaker into one or more chambers of the heart or attached to the outside of the heart to provide pacing therapy to the one or more chambers. As such, the example of FIGS. 4A-4C is illustrated for example purposes only and should not be considered limiting of the techniques described herein.

Figure 5:
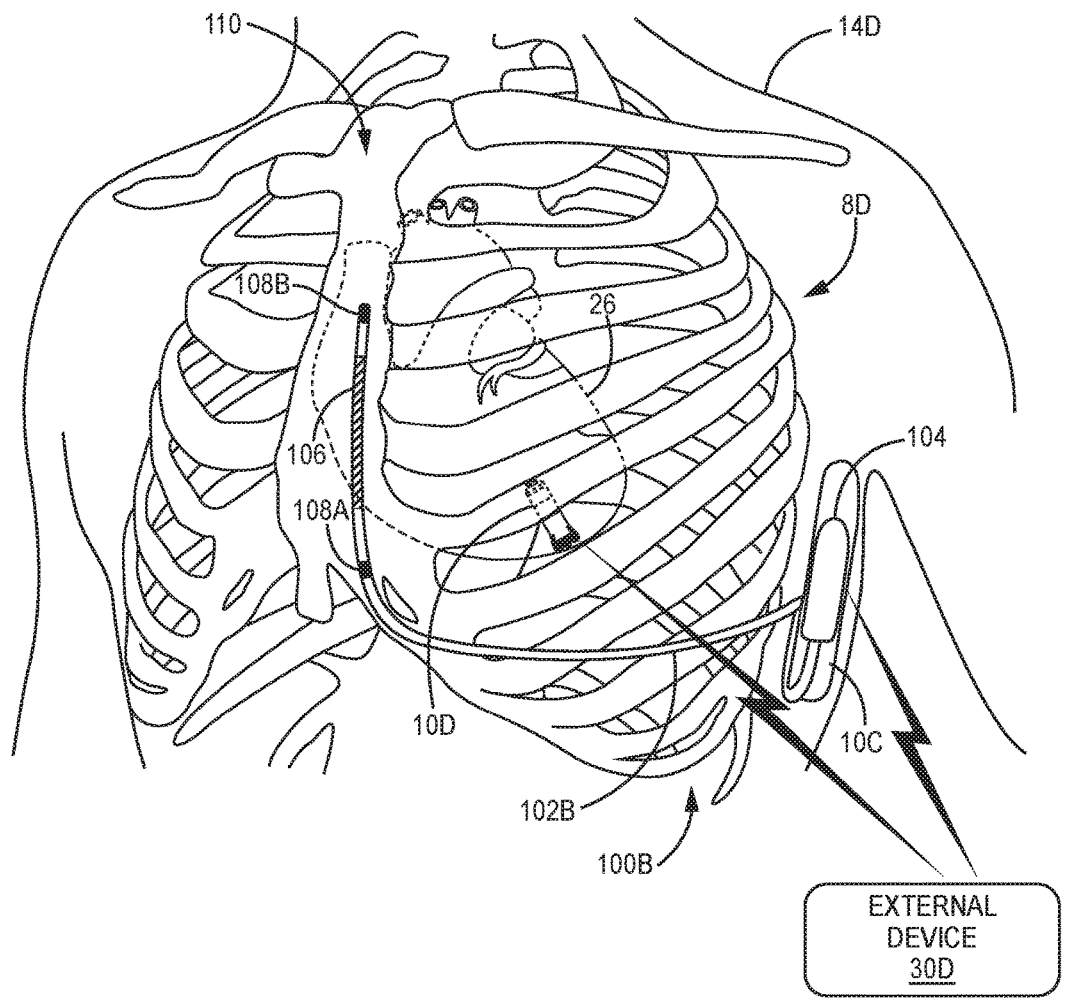
FIG. 5 is a conceptual drawing illustrating another example medical device system in conjunction with a patient.

FIG. 5 is a conceptual drawing illustrating another example medical device system 8D that includes an extracardiovascular ICD system 100B and IPD 10D implanted within a patient. Medical device system 8D may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A-4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., defibrillation electrodes 106A and 106B as illustrated in the example of FIGS. 4A-4C.

Figure 6:
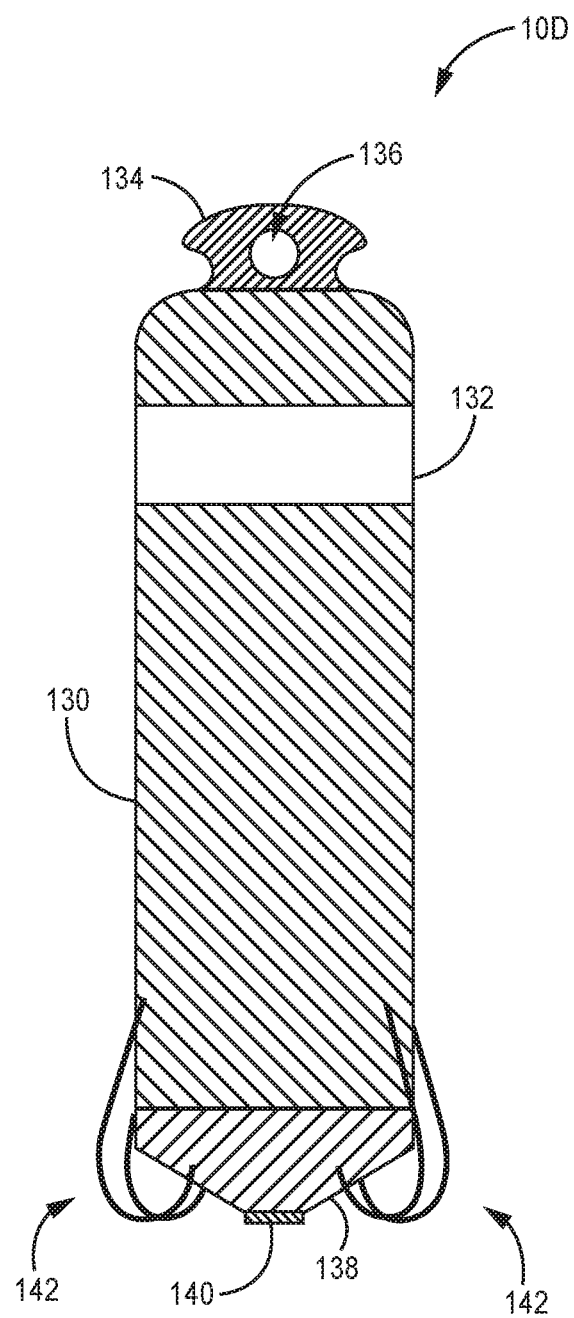
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140) to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 144 may be provided on one end of case 130 to enable tethering or extraction of IPD 10D. For example, a suture or other device may be inserted around flange 144 and/or through opening 146 and attached to tissue. In this manner, flange 144 may provide a secondary attachment structure to tether or retain IPD 10D within heart 16C (or 16D) if fixation mechanisms 142 fail. Flange 144 and/or opening 146 may also be used to extract IPD 10D once the IPD needs to be explanted (or removed) from patient 14D if such action is deemed necessary.

IPD 10D is one example of a pacing device configured to implement the techniques of this disclosure. However, other implantable medical devices may be used to perform the same or similar functions as IPD 10D. For example, an IPD may include a small housing that carries an electrode, similar to IPD 10D, and be configured to be implanted within a chamber of a heart 16. The IPD may also include one or more relatively short leads configured to place one or more respective additional electrodes at another location within the same chamber of the heart or a different chamber of the heart. In this manner, the housing of the IPD may not carry all of the electrodes used to perform functions described herein with respect to IPD 10D. In other examples, each electrode of the IPD may be carried by one or more leads (e.g., the housing of the IPD may not carry any of the electrodes). In some examples, an IPD or other pacing device may include or be coupled to three or more electrodes, where each electrode may deliver therapy and/or detect intrinsic signals.

In another example, a pacing device may be configured to be implanted external to the heart, e.g., near or attached to the epicardium of the heart. An electrode carried by the housing of the pacing may be placed in contact with the epicardium and/or one or more electrodes of leads coupled to the pacing may be placed in contact with the epicardium at locations sufficient to provide cardiac pacing. In still other examples, a pacing device configured to perform the techniques described herein may be implanted subcutaneously or submuscularly, and connected to one or more intracardiac leads carrying one or more electrodes.

Referring back to FIGS. 4A-5, medical device systems 8C and 8D are examples of medical device systems configured to determine whether a change in the cardiac function of a patient has occurred, and to responsively provide an alert indicating that a change in the cardiac function has occurred, and/or cause ICD 10C or IPD 10D to deliver therapy, or change the parameters of a therapy to be delivered based on the change in the patient's cardiac function indicated by medical device system 8C or 8D. The techniques may be performed by processing circuitry of medical device system 8C or 8D, such as processing circuitry of one or more of ICD 10C, IPD 10D, and external device 30C or 30D, individually, or collectively. Although the example medical devices systems 8C and 8D of FIGS. 4A-5 are illustrated as including both ICD 10C and IPD 10D, other examples may include only one of ICD 10C or IPD 10D, alone, or in combination with other implanted or external devices.

The techniques include determining a respective representative value for each of a plurality of patient heart rates and a nocturnal dip in the patient's heart rate during each of a plurality of periods, which may be at least one hour, such as approximately one day. The processing circuitry may determine the values of at least some the representative patient heart rates and the nocturnal dip in patient's heart rate based on physiological signals generated by sensing circuitry of one or both of ICD 10C and IPD 10D, such as cardiac EGM signals generated by sensing circuitry of the IMDs.

Figure 7:
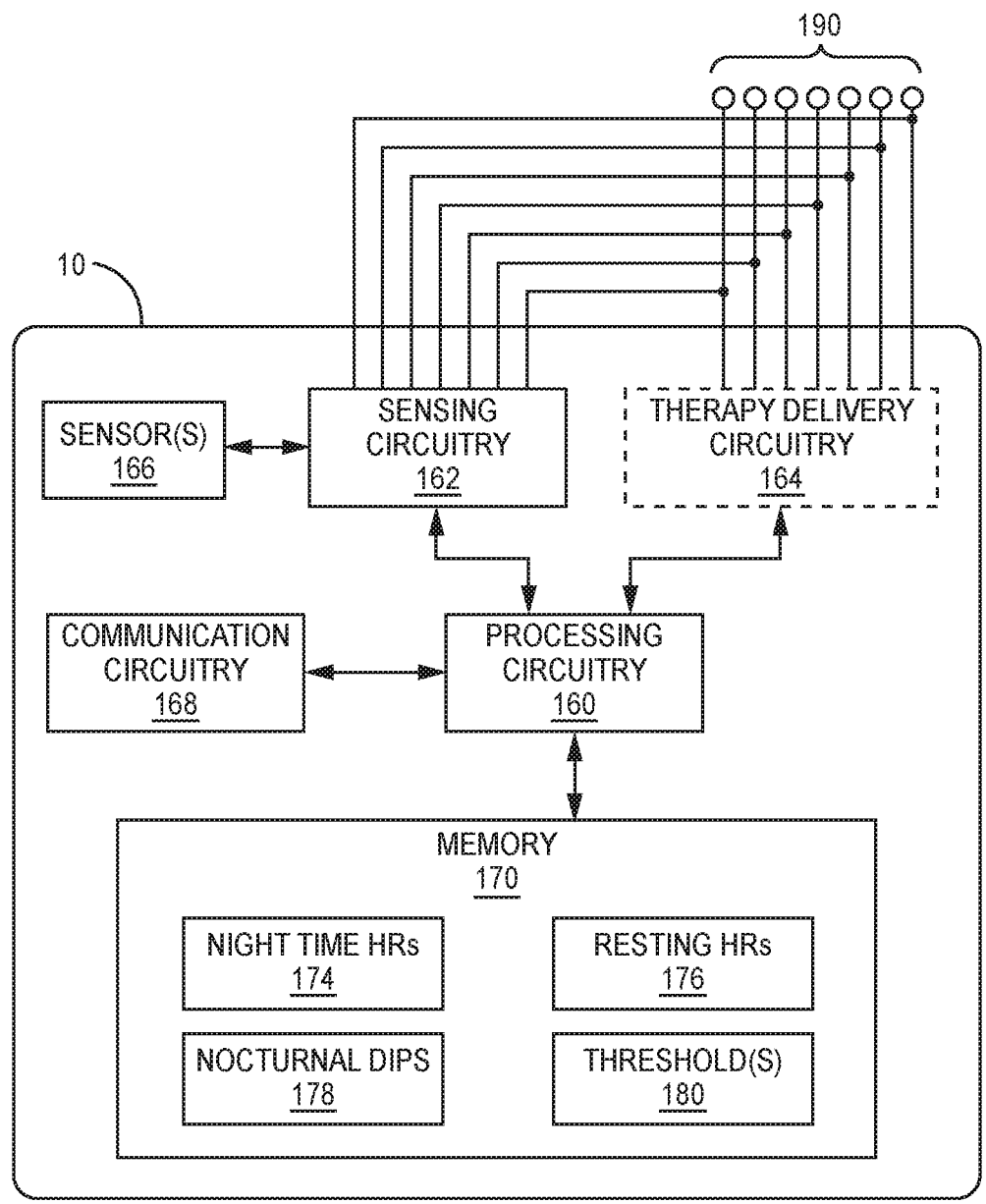
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement the techniques for determining whether a change in the cardiac function of a patient has occurred as described in this disclosure. In the illustrated example, IMD 10 includes processing circuitry 160 and an associated memory 170, sensing circuitry 162, therapy delivery circuitry 164, one or more sensors 166, and communication circuitry 168. However, ICD 10A, ICM 10B, ICD 10C, and IPD 10D need not include all of these components, or may include additional components. For example, ICM 10A may not include therapy delivery circuitry 164, in some examples.

Memory 170 includes computer-readable instructions that, when executed by processing circuitry 160, cause IMD 10 and processing circuitry 160 to perform various functions attributed to IMD 10 and processing circuitry 160 herein (e.g., determining patient parameter values, difference metrics, scores and thresholds, and determining whether to provide an alert indicating that an acute cardiac event is predicted). Memory 170 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 7 may correspond to, for example: electrodes 12, 22, 24, 25, 28, 44, and 44 of ICD 10A (FIG. 1); electrodes 64 and 66 of ICM 10B (FIG. 3); electrodes 106, 108, and one or more housing electrodes of ICD 10C (FIGS. 4A-5); or electrodes 132 and 140 of IPD 10D (FIG. 6).

Electrical sensing circuitry 162 monitors signals from a selected two or more of electrodes 190 in order to monitor electrical activity of heart 26, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 26. Indications of detected R-waves and P-waves may be used for determining heart rates and detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMD 10 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 160 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 160 in other examples.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 26. As another example, processing circuitry 160 may analyze the digitized cardiac electrogram signal to identify and measure a variety of morphological features of the signal. As described in greater detail below, the morphological features of the cardiac electrogram may be patient parameters, and their measurements patient parameter values, used to determine whether an acute cardiac event, e.g., ventricular tachyarrhythmia, is predicted to occur.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

According to the techniques for detecting a change in the cardiac function of a patient described herein, processing circuitry 160 determines a plurality of heart rates, e.g., based on indications of sensed R-waves and/or P-waves from sensing circuitry 162, during a period, such as a day. Each of the plurality of heart rates determined for the period may be a mean or median of heart rates determined during an interval, such as a minute. Processing circuitry 160 identifies a first subset of the heart rates as nighttime heart rates 174, e.g., if they occur during a first sub-period, which may be at night or when the patient is otherwise expected or determined to be sleeping, and a second subset of the heart rates as resting heart rates 176, e.g., if they occur during a second sub-period, which may be during the day or when the patient is otherwise expected or determined to be awake. In some examples, processing circuitry 160 identifies as resting heart rates those heart rates that occur during the second sub-period and when the patient is determined to be lying down and/or inactive. In some examples, sensors 166 of IMD 10 include one or more sensors that generate a signal that varies as a function of patient movement or posture, such as one or more accelerometers. Processing circuitry 160 may determine that patient 14 is inactive and/or lying down based on such signals.

For each period, processing circuitry 160 also determines a representative nighttime heart rate 174 and a representative resting heart rate 176. The representative nighttime heart rate 174 may be a minimum of the identified nighttime heart rates 174, or a mean or a median of the N lowest identified nighttime heart rates 174. In other examples, the representative nighttime heart rate 174 may be the minimum heart rate identified during the entire period, and may occur during either the first sub-period or second sub-period, e.g., at a time when the patient is determined to be lying down and/or inactive. The representative resting heart rate 176 for the period may be a minimum, mean or median of resting heart rates 176 identified during the period.

For each period, processing circuitry 160 also determines a nocturnal dip value 178 based on the representative nighttime heart rate 174 and the representative resting heart rate 176. The nocturnal dip values 178 may be determined based on a difference or ratio between the representative resting heart rate 176 and the representative nighttime heart rate 174. In some examples, the nocturnal dip values 178 may be the difference between the representative resting heart rate 176 and the representative nighttime heart rate 174 as a percentage of the resting heart rate, e.g., according to the equation, Nocturnal dip=100*(resting heart rate−nighttime heart rate)/resting heart rate.

Processing circuitry 160 also respective threshold values 180 for one or more of the nighttime heart rate, resting heart rate, and nocturnal dip, and compares the determined values for the period to the threshold values 180. The thresholds 180 may be predetermined values, or variable values determined based on one or more values of the parameter determined during one or more prior periods, e.g., a known baseline period or N preceding periods. Based on whether the current values of the parameters cross a threshold, processing circuitry may provide an alert.

Communication circuitry 168 includes any suitable hardware, firmware, software or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The clinician may also program parameters of IMD 10 using external device 30 or another local or networked computing device. In some examples, the clinician may select threshold values 180, and receive alerts based on comparison of heart rate parameters to thresholds as described herein.

Figure 8:
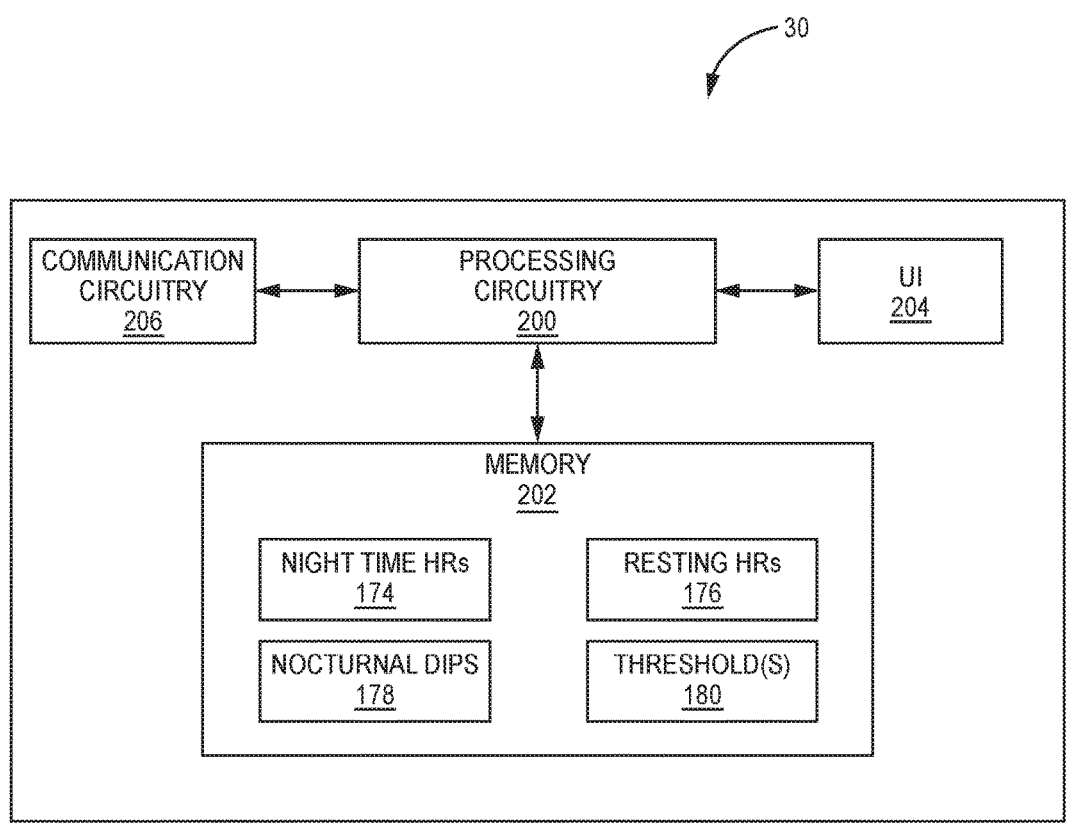
FIG. 8 is a functional block diagram illustrating an example configuration of an external device configured to communicate with one or more implantable medical devices.

FIG. 8 is a functional block diagram illustrating an example configuration of an external device 30 configured to communicate with one or more IMDs 10. In the example of FIG. 8, external device 30 includes processing circuitry 200, memory 202, user interface (UI) 204, and communication circuitry 206. External device 30 may correspond to any of external devices 30A-30C described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., running an application that enables external device 30 to program and/or interrogate IMD 10.

In some examples, a user uses external device 30 to select or program any of the values for operational parameters of IMD 10, e.g., for patient parameter sensing, therapy delivery, and acute cardiac event prediction. In some examples, a user uses external device 30 to receive data collected by IMD 10, such as heart rate and nocturnal dip values, or other operational and performance data of IMD 10. The user may also receive alerts provided by IMD 10 that indicate that the heart rate or nocturnal dip crossed a threshold indicating a change in cardiac health. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive heart rates determined by an IMD 10 and determine periodic representative night time heart rates 174 and resting heart rates 176, nocturnal dips 178, and thresholds 180. Processing circuitry 200 may compare the periodic values to the thresholds to determine whether to provide the user an alert, as described herein.

Figure 9:
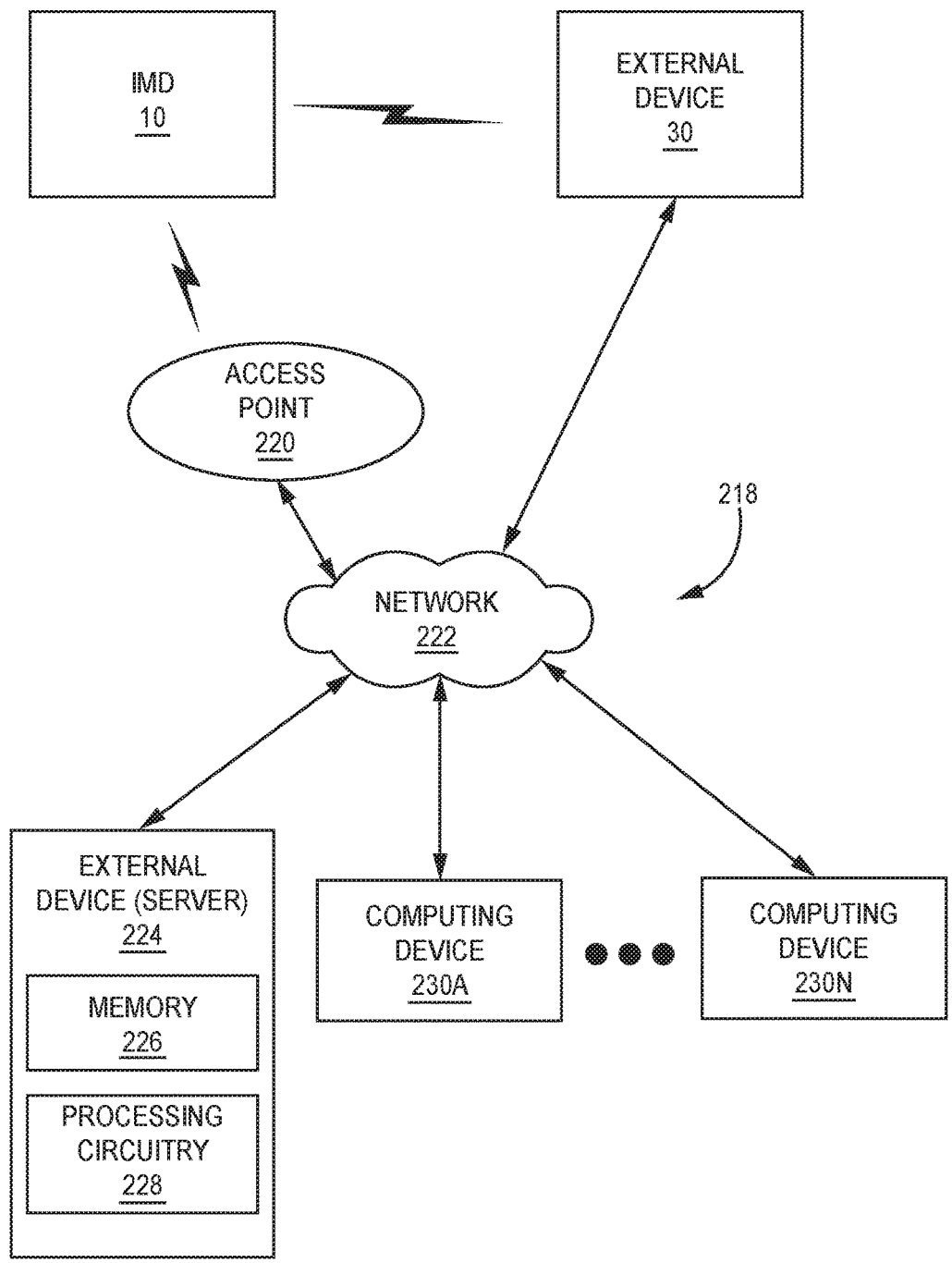
FIG. 9 is a functional block diagram illustrating an example system that includes remote computing devices, such as a server and one or more other computing devices, that are connected to an implantable medical device and/or external device via a network.

FIG. 9 is a functional block diagram illustrating an example system that includes external computing devices, such as a server 224 and one or more other computing devices 230A-230N, that are coupled to IMD 10 and external device 30 via a network 222. In this example, IMD 10 may use its communication module 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, patient parameter values 174, difference metrics 176, scores 178, thresholds 180, alerts of changes in cardiac function, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, relating to evaluation of cardiac condition based on nighttime and resting heart rates, and nocturnal dip. Processing circuitry 228 may provide an alert to a user via network 222, e.g., via external device 30 or one of computing devices 170.

Figure 10:
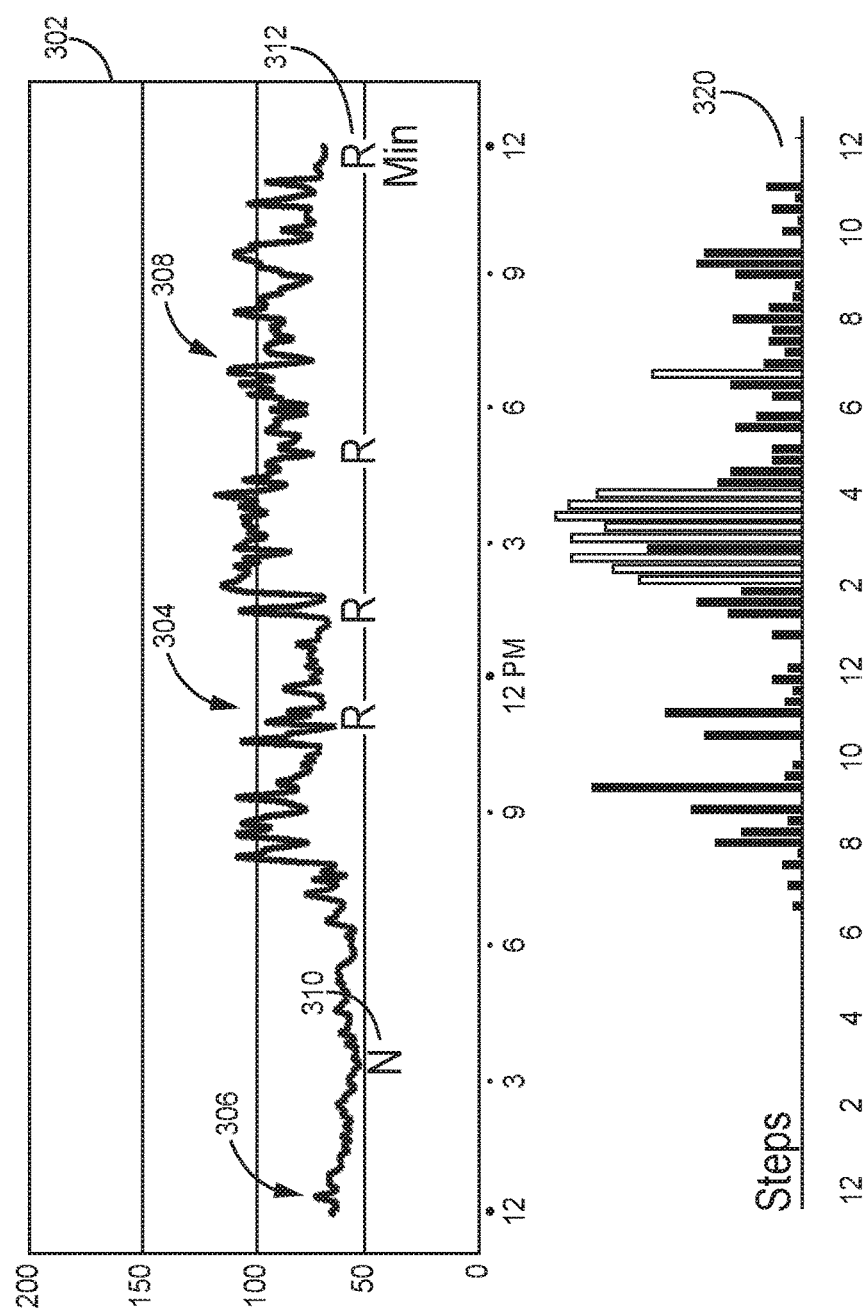
FIG. 10 is a conceptual diagram illustrating an automatically determined heart rate of a patient during a period in conjunction with an indication of activity of the patient during the period.

FIG. 10 is a conceptual diagram illustrating an automatically determined heart rate of a patient during a period in conjunction with an activity level of the patient during the period. Chart 302 illustrates the heart rate of a patient during a period 304, which in this example equals approximately one day. The heart rate of the patient may be sensed by sensing circuitry 162 at predetermined intervals, such as at intervals equaling approximately one minute. As discussed below in greater detail, processing circuitry 160 may analyze the heart rate during period 304 and identify heart rates determined during a first sub-period 306 as nighttime heart rates and heart rates determined during a second sub-period 308 as daytime heart rates. Within first sub-period 306, processing circuitry 160 may further analyze the heart rates in order to determine a representative nighttime heart rate 310 for period 304, which may comprise the lowest value ("N") sensed during first sub-period 306. Within second sub-period 308, processing circuitry 160 may analyze the heart rates in order to identify a plurality of resting heart rates R, which may be identified during periods of relative patient inactivity. As described above, the medical device systems described herein may further include sensors 166, such as accelerometers, that generate physiological signals that vary based on patient motion and/or posture. Thus, by incorporating physiological signals obtained from sensors such as accelerometer 166, processing circuitry 160 may also determine a representative resting heart rate 312 for the period, which may comprise the lowest value ("RMin") sensed during the portions of second sub-period 308 in which the patient was relatively inactive. In addition, in some examples, processing circuitry 160 may determine whether a current sub-period of a period comprises a first sub-period or a second sub-period based on other types of patient motion and/or posture.

Chart 320 of FIG. 10 illustrates the relative number of steps taken by the patient during the period. In some examples, processing circuitry 160 may identify a heart rate sensed during an interval of subset 308 as a resting heart rate only if the patient is relatively inactive. For example, a heart rate sensed during an interval of second sub-period 308 may not be identified as a resting heart rate if the patient had taken more than a predetermined threshold number of steps during a predetermined number of preceding intervals. By excluding periods of physical activity from the identification of the plurality of resting heart rates R, processing circuitry 160 may be better able to determine a representative resting heart rate 312 for the period, since a patient's heart rate may increase significantly during periods of physical activity, as illustrated by the correlation between the heart rate during period 304 and the number of steps shown in chart 320 for a given point in time, e.g., around 3:30 p.m. in the example charts 302 and 320 shown in FIG. 10.

FIGS. 11A-14 are flow diagrams illustrating example techniques that may be implemented by a medical device system 8, e.g., processing circuitry of the medical device system, to automatically determining whether a change in a patient's cardiac function has occurred, based on one or more parameters of the patient's heart rate including a representative resting heart rate, a representative nighttime heart rate, and a nocturnal dip in heart rate, and providing an alert indicating that a change in cardiac function has occurred. The flowcharts of FIGS. 11A-14 are intended to illustrate the functional operation of an IMD 10, external device 30, medical system 8, and other devices and systems described herein, and should not be construed as reflective of a specific form of software or hardware necessary to practice the methods described. Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

The example methods illustrated by FIGS. 11A-14 may be performed, by any one or more devices described herein, and may be performed, in part, by processing circuitry of any one or more devices described herein, such as by processing circuitry 160 of IMD 10 (which may correspond to any of ICD 10A, ICM 10B, ICD 10C, IPD 10D, or any other IMD), processing circuitry 200 of external device 30, processing circuitry 228 of server 224. For ease of description, the methods of FIGS. 11A-14 will be described hereafter as being performed by processing circuitry 160 of IMD 10.

Figure 11A:
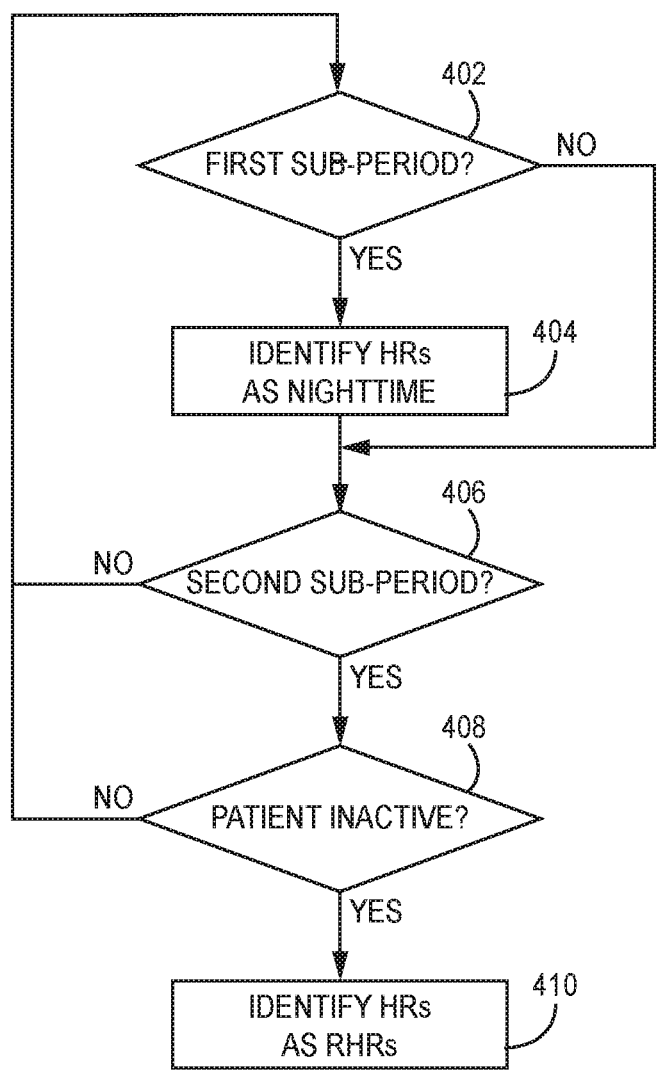
FIG. 11A is a flow diagram illustrating an example technique that may be implemented by a medical device system to automatically monitor and store heart rate data of a patient as a nighttime heart rate data during a first sub-period, and to store heart rate data of a patient as resting heart rate data during a second sub-period when the patient is inactive.

FIG. 11A is a flow diagram illustrating an example technique that may be implemented by the processing circuitry of any of the medical device systems described herein to automatically monitor and store heart rate data based on at least one of the current sub-period and patient activity level. For example, processing circuitry 160 may store heart rate data as nighttime heart rate data during a first sub-period. Processing circuitry 160 may store heart rate data as resting heart rate data during portions of a second sub-period when the patient is relatively inactive. According to the example method of FIG. 11A, processing circuitry 160 determines whether a current interval of the period corresponds to the first sub-period (402). If processing circuitry 160 determines that the current interval of the period corresponds to the first sub-period, then processing circuitry 160 identifies the heart rate determined at the current interval as a nighttime heart rate (404).

Once processing circuitry 160 has identified the heart rate as a nighttime heart rate, processing circuitry 160 may store the value for the heart rate as a nighttime heart rate for the period. Alternatively, if processing circuitry 160 determines that the current interval of the period does not correspond to the first sub-period, then processing circuitry 160 determines whether the current interval of the period corresponds to the second sub-period (406). If processing circuitry 160 determines that the current interval of the period corresponds to the second sub-period, then processing circuitry 160 determines whether the physiological signals of the patient indicate that the patient also is inactive (408). At block 410, physiological signals indicative of patient inactivity may include, for example, signals received from a motion sensor. Example motion sensors may include accelerometer 166 of IMD 10. Signals from the motion sensor may indicate patient motion, such as a number of steps taken by the patient during the current and/or preceding intervals. However, it is contemplated that patient motion or activity levels may be defined in other ways than a number of steps, as, for example, in the case of patients using a wheelchair or who otherwise are not ambulatory. If processing circuitry 160 determines that the current interval corresponds to the second sub-period and that the patient is also inactive, then processing circuitry 160 identifies the heart rate of the patient determined at the current interval as a resting heart rate and stores corresponding value as a resting heart rate for the period. The example method of FIG. 11A may be performed for each of a plurality of consecutive intervals within a period, and may be performed for each of a plurality of periods. Intervals may have a length of approximately one minute, for example, and periods may have a length of approximately one day.

Figure 11B:
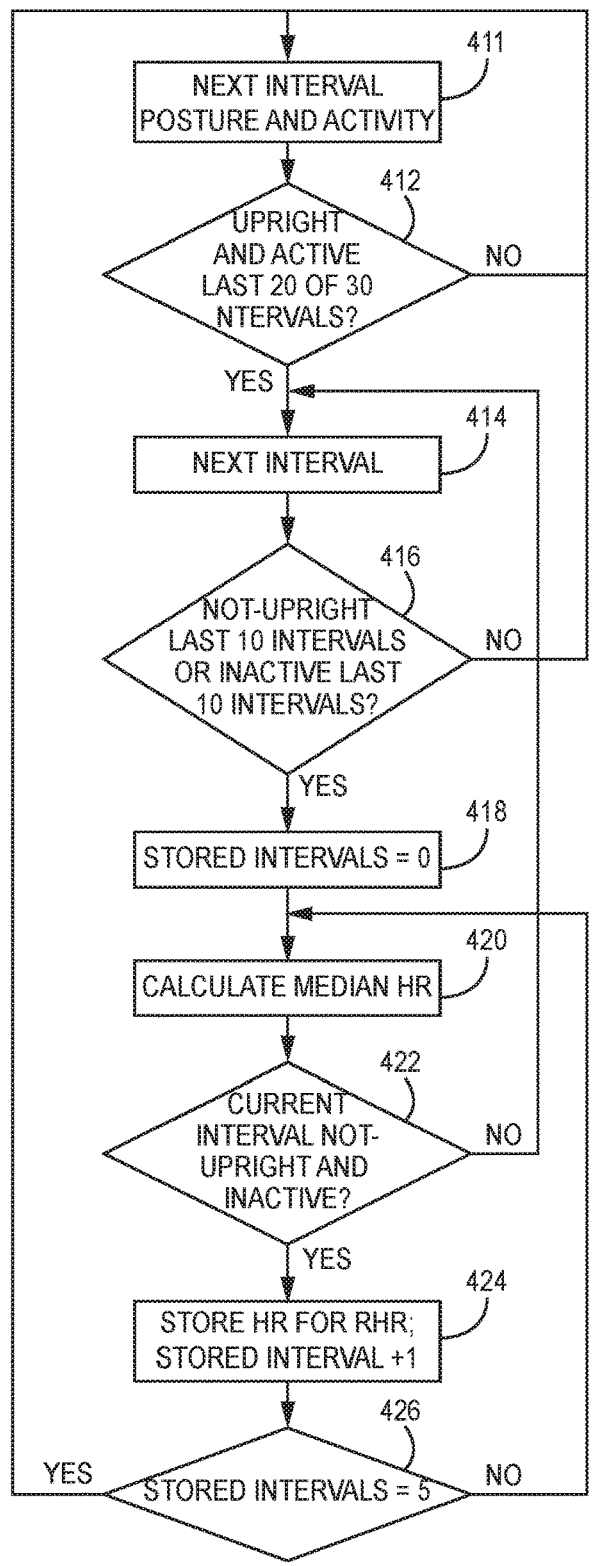
FIG. 11B is a flow diagram illustrating an example technique that may be implemented by a medical device system to determine and store heart rate data of a patient during portions of the second sub-period when the patient is inactive and/or not in an upright position.

FIG. 11B is a flow diagram illustrating an example technique that may be implemented by a medical device system to determine and store heart rate data of a patient during portions of the second sub-period of time, e.g., a daytime sub-period, based on both the patient's activity level and posture. The example method of FIG. 11B may begin, for example, at a particular time of day when the patient is likely to be awake. According to the example of FIG. 11B, processing circuitry 160 determines whether the patient has been upright and active during twenty of the past thirty intervals (412). If the patient has been upright and active during twenty of the past thirty intervals (YES of 412), then the method proceeds (414) to block 416, in which processing circuitry 160 determines whether the patient has been at least one of inactive for the past ten intervals or in a not-upright position for the past ten intervals (416). For example, accelerometer 166 of IMD 10 may be capable of sensing motion along multiple axes, and thereby may sense patient posture. In some examples, processing circuitry 160 may determine that the patient is in an upright or not-upright position if signals from accelerometer 166 indicate a patient posture greater or less than an angle of a predetermined number of degrees, e.g., 60 degrees. In addition, as discussed above with respect to FIG. 11A, signals from accelerometer 166 may comprise motion data indicating the activity of the patient during the current and/or preceding intervals, and activity greater or less than a threshold may indicate whether the patient is inactive or active.

A determination that the patient has been upright and active during a threshold number, fraction, or percentage of previous intervals (YES of 412) may indicate that the patient has begun daytime/waking activity. This determination may be used, e.g., with time of day, to indicate the beginning of the second sub-period during which resting heart rates may be determined by detecting periods of daytime/waking inactivity (416-426). If the patient has not been determined to have been upright and active during a threshold number, fraction, or percentage of previous intervals (NO of 412), processing circuitry 160 may continue to monitor activity and/or posture during intervals (411) until this condition is satisfied.

If the patient has been at least one of inactive or in a not-upright position for the past ten intervals (YES of 416), then processing circuitry determines that a stored-interval courter=0 at block 418, and calculates the median heart rate for the current interval (420). Processing circuitry 160 then determines whether the patient has remained inactive and not-upright during the current interval (YES of 422), stores the median heart rate for the current interval as a "resting heart rate" value, and increases the stored-interval counter by a discrete value such as +1 (424).

If the patient remains inactive and in a not-upright position, then processing circuitry 160 repeats steps 420 through 426 until the value of the stored-interval counter reaches a predetermined value; e.g., a value representing that resting heart rate values have been stored for each of the past five intervals. If the patient does not remain inactive and in a not-upright position until the stored-interval counter reaches the predetermined value (NO at 422), then the method returns to block 414, at which processing circuitry 160 determines whether the patient has been at least one of inactive for the past ten intervals or in a not-upright position for the past ten intervals. If the patient has not been at least one of inactive or in a not-upright position for the past ten intervals, then the method returns to the beginning step of determining the activity and posture of the patient at the next interval (410).

Figure 12:
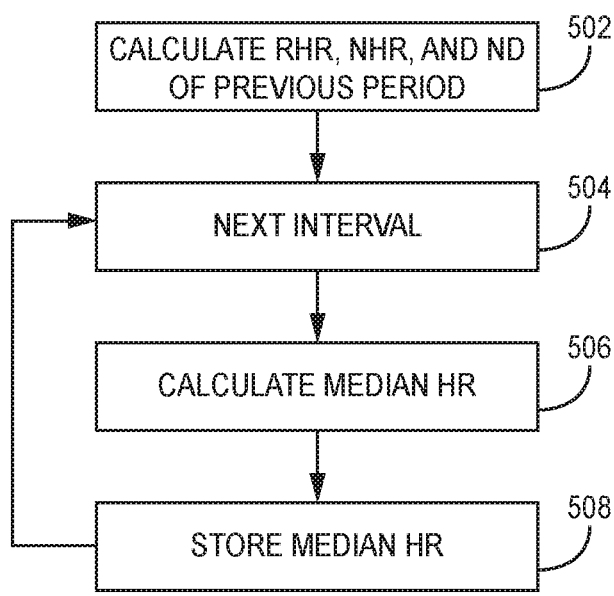
FIG. 12 is a flow diagram illustrating an example technique that may be implemented by a medical device system to calculate values representative of a heart rate of the patient during the preceding period, and then determine and store heart rate data of a patient during a second sub-period of time.

FIG. 12 is a flow diagram illustrating an example technique that may be implemented by a medical device system at the beginning of a first sub-period of a period to determine values representative of a heart rate of the patient during the preceding period, e.g., during the preceding 24 hours (day). In some examples, at the beginning of the first sub-period of a period, e.g., at a time of each day associated with night or sleeping, processing circuitry 160 may finalize the values to store for the preceding period. For example, at block 502, processing circuitry may calculate a representative resting heart rate (RHR), a representative nighttime heart rate (NHR), and a nocturnal dip in heart rate (ND) for the previous period. As discussed above with respect to FIGS. 10-11B, the representative resting heart rate may comprise the lowest value for the resting heart rates saved during the portions of the second sub-period of the previous period in which the patient was at least one of inactive and/or in a not-upright position, whereas the representative nighttime heart rate may comprise the lowest value for the nighttime heart rates saved during the first sub-period of the previous period.

The value for the nocturnal dip in the patient's heart rate for the previous period (502) may be calculated based on the representative resting heart rate for the previous period and the representative nighttime heart rate for the previous period. For example, the nocturnal dip may comprise the difference between the representative resting heart rate and the representative nighttime heart rate. In other examples, the nocturnal dip may comprise a percentage by which the representative nighttime heart rate differs from the representative resting heart rate. A percentage value for the nocturnal dip may be obtained by the following equation:

$$\text{nocturnal dip}=100*(RHR-NHR)\div RHR \quad \text{(Eq. 1)}$$

After the processing circuitry 160 has calculated the representative resting heart rate, representative nighttime heart rate, and nocturnal dip of the previous period (502), the example technique of FIG. 12 further includes proceeding to a next interval of the first sub-period of the current period (504), calculating the median heart rate for that interval (506), and storing the calculated median heart rate (508). In some examples, the steps of blocks 504 through 508 may then repeat for successive intervals until the end of the first sub-period of the current period.

Figure 13:
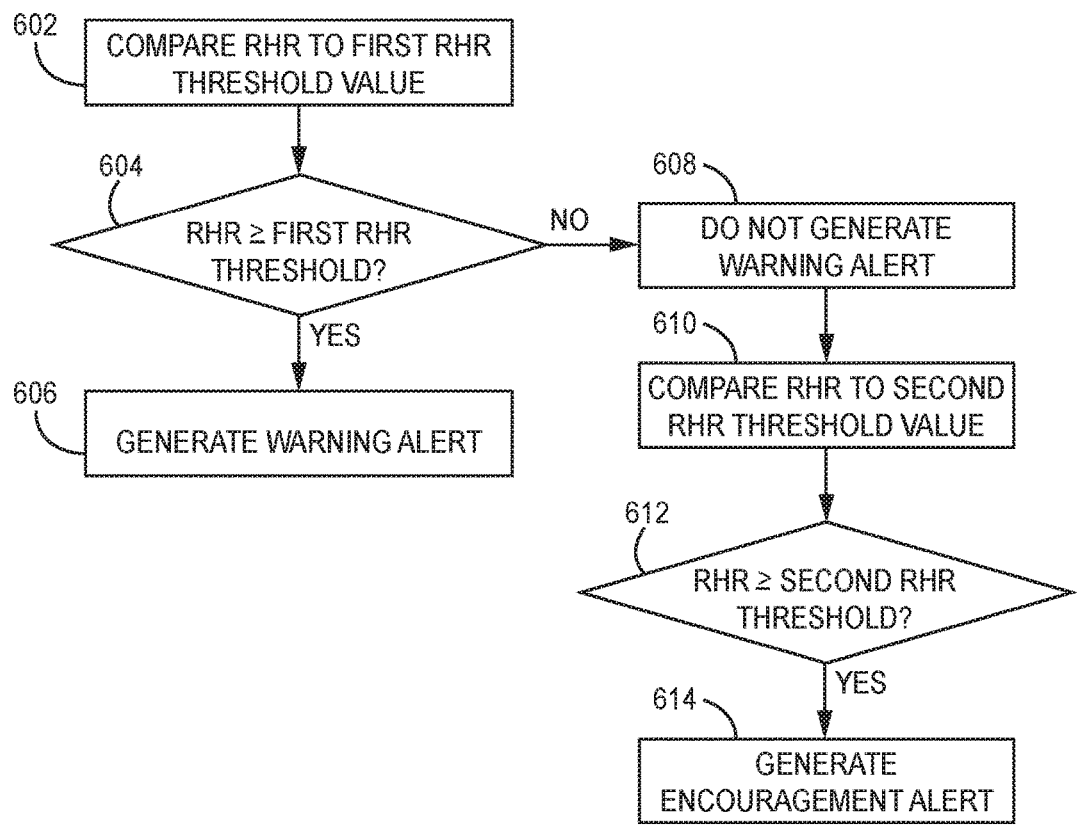
FIG. 13 is a flow diagram illustrating an example technique that may be implemented by a medical device system to determine whether to generate an alert based on comparing resting heart rate data to one or more threshold values and determining whether a change in the patient's cardiac function has occurred.

FIG. 13 is a flow diagram illustrating an example technique that may be implemented by a medical device system to determine whether to generate an alert based on comparing a representative resting heart rate to one or more threshold values and determining, based on the comparison whether a change in the patient's cardiac function has occurred. Resting heart rate, like nocturnal dip, can also provide objective measures of cardiac health. Generally, a resting heart rate that is relatively high indicates a lower degree of cardiac health than a resting heart rate that is relatively low. As will be apparent to those skilled in the art, a patient's resting heart rate may change over time. An increase in the patient's resting heart rate may be indicative of worsening cardiac health and/or a decrease in cardiovascular fitness or general health such as a fever. A decrease in the patient's resting heart rate may be indicative of improved cardiac health and/or an increase in cardiovascular fitness. For example, physical exercise may strengthen the cardiac muscle, thereby necessitating fewer beats per minute and decreasing the resting heart rate. Thus, patients may be able to exert some degree of control over their resting heart rates by engaging in physical exercise. In order to encourage patients to engage in physical exercise, processing circuitry 160 may generate both warning alerts (606) and encouragement alerts (614) based on determinations that a representative resting heart rate is above or below a threshold value.

At block 602 of FIG. 13, processing circuitry 160 compares the representative resting heart rate to a first threshold value. For example, the first threshold value may be a fixed threshold, such as a predetermined "beats-per-minute" value. In some examples, the first threshold may be approximately 100 beats per minute, although other values are contemplated that may be predetermined for a specific patient. In other examples, the first threshold may comprise a percentage by which the representative resting heart rate for the current period differs from the representative resting heart rate determined for one or more previous periods. If the representative resting heart rate equals or exceeds the first threshold value (YES at 604), then processing circuitry 160 may generate a warning alert (606). In some examples, the warning alert may be transmitted by processing circuitry 160 to network 222 and then to external device 30. External device 30 may produce a visual, auditory, or tactile warning signal that alerts a user, such as a patient or clinician, to the determination that the representative resting heart rate is equal to or greater than the first threshold. In some examples, the determination that the resting heart rate has equaled or exceeded the first threshold (604) may be stored in memory 226, and/or form the basis for modifying parameters of therapy to be delivered to the patient by an outside device such as ICD 10C, IPD 10D, or any other IMD capable of delivering therapy to the patient.

At block 604, if processing circuitry 160 determines that the representative resting heart rate does not equal or exceed the first threshold (No at 604), no warning alert is generated, and the method progresses to block 610, at processing circuitry compares the representative resting heart rate to a second threshold value. For example, the second threshold value may also be a predetermined "beats-per-minute" value, such as approximately 70 beats per minute. The predetermined beats-per-minute value may be based on factors such as a patient's age and/or level of physical conditioning, or the predetermined beats-per-minute value may be based on representative resting heart rate values calculated for past periods. If the representative resting heart rate equals or is lower than the second threshold value (YES at 612), then processing circuitry may generate an encouragement alert (614). In some examples, the encouragement alert may be transmitted by processing circuitry 160 to network 222 and then to external device 30. External device 30 may produce a visual, auditory, or tactile encouragement signal that alerts a user, such as a patient or clinician, to the determination that the representative resting heart rate is equal to or less than the second threshold. In some examples, the encouragement alert may comprise a message intended to encourage the patient to maintain or increase engagement in physical exercise to improve cardiac function.

In other examples, the first threshold value and the second threshold value for the representative resting heart rate may comprise, respectively, a first and second mean or median of the representative resting heart rate determined for one or more previous periods. For example, processing circuitry 160 may determine whether the representative resting heart rate is at least one of equal to, less than, or greater to a predetermined mean or median value for five out of the previous seven periods. In some examples, the mean or median value may comprise a "beats-per-minute" value, such as approximately 100 beats per minute, although other mean or median values are contemplated that may be predetermined for a specific patient. If processing circuitry 160 determines that the representative resting heart rate is equal to or greater than the first predetermined mean or median value of the representative resting heart rate determined for the one or more previous periods (YES at 604), then a warning alert is generated as described above with respect to block 606. Similarly, if processing circuitry 160 determines that the representative resting heart rate is equal to or less than the second predetermined mean or median value of the representative resting heart rate determined for the one or more previous periods (YES at 612), then an encouragement alert is generated as described above with respect to block 614.

Figure 14:
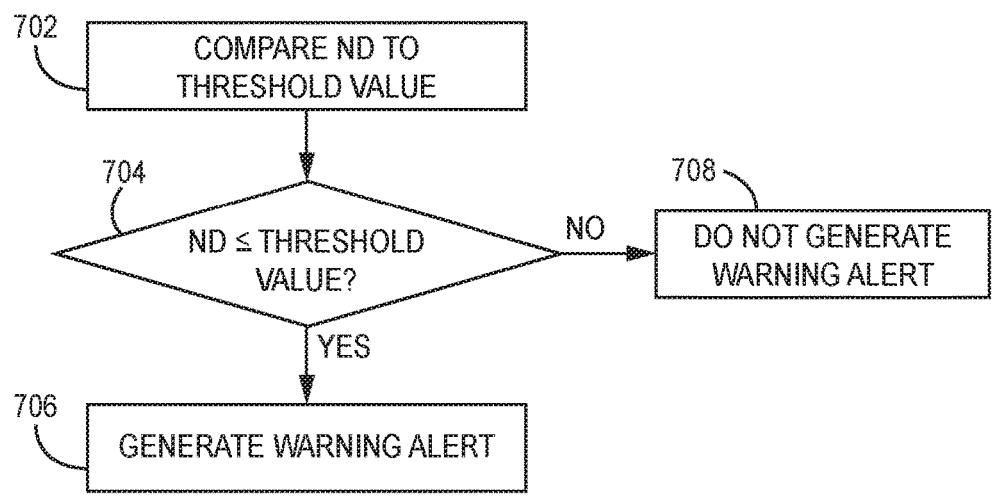
FIG. 14 is a flow diagram illustrating an example technique that may be implemented by a medical device system to determine whether to generate an alert based on comparing a nocturnal dip to one or more threshold values and determining whether a change in the patient's cardiac function has occurred.

FIG. 14 is a flow diagram illustrating an example technique that may be implemented by a medical device system to determine whether to generate an alert based on comparing a nocturnal dip to one or more threshold values and determining whether a change in the patient's cardiac function has occurred. At block 702 of FIG. 14, processing circuitry 160 compares the nocturnal dip to a threshold value. The threshold value may, for example, be a predetermined based on the values of the nocturnal dip determined by processing circuitry 160 for one or more previous periods. In some examples, the threshold value may comprise a predetermined percentage value by which the representative nighttime heart rate differs from the representative resting heart rate.

If processing circuitry 160 determines that the nocturnal dip is equal to or less than the threshold value, (YES at 704), then processing circuitry 160 may generate a warning alert (706). In some examples, the warning alert may be transmitted by processing circuitry 160 to network 222 and then to external device 30. External device 30 may produce a visual, auditory, or tactile warning signal that alerts a user, such as a patient or clinician, to the determination that the nocturnal dip is equal to or less that the threshold. In some examples, the determination that the nocturnal dip is equal to or less than the threshold (704) may be stored in memory 226, and/or form the basis for modifying parameters of therapy to be delivered to the patient by an outside device such as ICD 10C, IPD 10D, or any other IMD capable of delivering therapy to the patient. If processing circuitry 160 determines that the nocturnal dip is not equal to or less than the threshold value, then no warning alert is generated (708).

In other examples of FIG. 14, processing circuitry 160 may determine whether to generate an alert based on determining whether the nocturnal dip is equal to or less than a predetermined percentage value during one or more previous periods, and further based on determining that the number of times that the nocturnal dip was equal to or less than a threshold value during the one or more previous periods is equal to or greater than a predetermined number of times (704). For example, processing circuitry 160 may determine whether the nocturnal dip was equal to or less than 10% for five or more out of the past seven periods. If processing circuitry 160 determines that the nocturnal dip was equal to or less than a predetermined percentage value during the one or more previous periods, and further determines that the number of times that the nocturnal dip was equal to or less than a threshold value during the one or more previous periods is equal to or greater than a predetermined number of times (YES at 704), then a warning alert is generated, as described above with respect to block 706. Alternatively, if processing circuitry 160 determines that the nocturnal dip was not equal to or less than equal to or less than a predetermined percentage value during the one or more previous periods, or determines that the number of times that the nocturnal dip was equal to or less than a threshold value during the one or more previous periods is not equal to or greater than a predetermined number of times (NO at 704), then a warning alert is not generated, as described above with respect to block 708.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Exemplary Embodiments

Embodiment 1 is a method comprising:
generating, by sensing circuitry configured to sense a cardiac electrogram signal of a patient via a plurality of electrodes, a signal that varies as a function of movement and posture of the patient; and
for each of a plurality of periods, by processing circuitry:
determining a plurality of heart rates of the patient based on the cardiac electrogram signal;
identifying a first subset of the plurality of heart rates as nighttime heart rates;
identifying a second subset of the plurality of heart rates as resting heart rates;
determining a representative nighttime heart rate based on the first subset of the plurality of heart rates;
determining a representative resting heart rate based on the second subset of the plurality of heart rates;
determining a nocturnal dip based on the representative nighttime heart rate and the representative resting heart rate;
comparing at least one of the representative nighttime heart rate, the representative resting heart rate, and the nocturnal dip to a respective threshold value; and
determining whether to generate an alert indicating a change in the cardiac function of the patient based on the comparison.

Embodiment 2 is the method of embodiment 1, wherein the plurality of heart rates comprise heart rates determined, by the processing circuitry, at predetermined intervals during a plurality of sub periods, wherein the plurality of sub-periods comprises:
a first sub-period, wherein the first subset of nighttime heart rates are heart rates determined during the first sub-period; and
a second sub-period, wherein the second subset of resting heart rates are heart rates determined during the second sub-period.

Embodiment 3 is the method of embodiment 2, wherein the second subset of resting heart rates are heart rates of the plurality of heart rates that were determined, by the processing circuitry, during the second sub-period when the one or more physiological signals of a patient indicate that the patient is inactive.

Embodiment 4 is the method of embodiment 2, wherein the second subset of resting heart rates are heart rates of the plurality of heart rates that were determined, by the processing circuitry, during the second sub-period when the one or more physiological signals of a patient indicate that the patient is inactive and in a not-upright position.

Embodiment 5 is the method of embodiment 4, further comprising determining whether the patient was at least one of upright or active for a threshold amount of time during the second sub-period based on the one or more physiological signals of the patient, wherein the second subset of resting heart rates are heart rates of the plurality of heart rates that were determined during the second sub-period when the one or more physiological signals of a patient indicate that the patient is inactive and in a not-upright position after having been upright or active for the threshold amount of time.

Embodiment 6 is the method of any of embodiments 1 to 5, wherein the intervals comprise approximately one minute.

Embodiment 7 is the method of any of embodiments 1 to 6, wherein the representative resting heart rate comprises a minimum value of the second subset of the plurality of heart rates identified, by the processing circuitry, as resting heart rates.

Embodiment 8 is the method of any of embodiments 1 to 7, wherein the representative nighttime heart rate comprises a minimum value of the first subset of the plurality of heart rates identified, by the processing circuitry, as nighttime heart rates.

Embodiment 9 is the method of any of embodiments 1 to 8, wherein the nocturnal dip comprises a value by which the representative nighttime heart rate differs from the representative resting heart rate.

Embodiment 10 is the method of any of embodiments 1 to 9, further comprising generating, by the processing circuitry, an alert based on:
comparing the representative resting heart rate to the respective threshold value, wherein the respective threshold value comprises a predetermined number of beats per minute; and
determining that the representative resting heart rate is at least one of equal to or greater than the predetermined number of beats per minute.

Embodiment 11 is the method of any of embodiments 1 to 10, further comprising generating, by the processing circuitry, an alert based on:
comparing the representative resting heart rate to the respective threshold value, wherein the respective threshold value is based on at least one of a mean or median of the representative resting heart rate determined for one or more previous periods; and
determining that the representative resting heart rate is at least one of equal to or greater than the respective threshold value.

Embodiment 12 is the method of any of embodiments 1 to 11, further comprising generating, by the processing circuitry, an alert based on:
comparing the nocturnal dip to the respective threshold value, wherein the respective threshold for the nocturnal dip is based on values of nocturnal dip determined for one or more previous periods; and
determining that the nocturnal dip is at least one of equal to or less than the respective threshold value.

Embodiment 13 is the method of any of embodiments 1 to 12, further comprising generating, by the processing circuitry, an alert based on:
determining whether the nocturnal dip was equal to or less than a predetermined percentage value during one or more previous periods; and
determining that the number of times that the nocturnal dip was equal to or less than the respective threshold value during the one or more previous periods is at least one of equal to or greater than the predetermined number of times.

Embodiment 14 is the method of embodiment 13, wherein the threshold value comprises a predetermined percentage value by which the representative nighttime heart rate differs from the representative resting heart rate.

Embodiment 15 is the method of any of embodiments 1 to 14, further comprising an implantable medical device, wherein the implantable medical device comprises a housing configured for implantation in the patient, wherein the housing includes the sensing circuitry and the processing circuitry.

Embodiment 16 is the method of embodiment 15, wherein the housing of the implantable medical device further includes a plurality of electrodes coupled to the sensing circuitry, and wherein the sensing circuitry is configured to generate a subcutaneous cardiac electrogram based on cardiac signals sensed via the electrodes.

Embodiment 17 is a medical device system comprising means for performing any of the methods of embodiments 1 to 16.

Embodiment 18 is a non-transitory computer-readable storage medium comprising instructions, that when executed by processing circuitry of a medical device system, cause the medical device system to perform any of the methods of embodiments 1 to 16.

Various aspects of the disclosure have been described. These and other aspects are within the scope of the following claims.

What is claimed is:

1. A medical device system comprising:
sensing circuitry configured to sense a cardiac electrogram signal of a patient via a plurality of electrodes and generate a signal that varies as a function of movement and posture of the patient; and
processing circuitry configured to, for each of a plurality of periods:
determine a plurality of heart rates of the patient based on the cardiac electrogram signal;
identify a first subset of the plurality of heart rates as nighttime heart rates, wherein each of the first subset of the plurality of heart rates occur when the patient is expected or determined to be asleep;
identify a second subset of the plurality of heart rates as resting heart rates, wherein each of the second subset of the plurality of heart rates occur when the patient is expected or determined to be awake and when at least one of the patient is lying down or an activity level of the patient satisfies a patient inactivity threshold;
determine a representative nighttime heart rate based on the first subset of the plurality of heart rates;
determine a representative resting heart rate based on the second subset of the plurality of heart rates;
determine a nocturnal dip based on the representative nighttime heart rate and the representative resting heart rate;
compare at least one of the representative nighttime heart rate, the representative resting heart rate, and the nocturnal dip to a respective threshold value; and
determine whether to generate an alert indicating a change in the cardiac function of the patient based on the comparison.

2. The system of claim 1, wherein each of the plurality of periods comprises approximately one day.

3. The system of claim 1, wherein the plurality of heart rates comprise heart rates determined at predetermined intervals during a plurality of sub periods, wherein the plurality of sub-periods comprises:
a first sub-period, wherein the first subset of nighttime heart rates are heart rates determined during the first sub-period; and
a second sub-period, wherein the second subset of resting heart rates are heart rates determined during the second sub-period.

4. The system of claim 3, wherein the second subset of resting heart rates are heart rates of the plurality of heart rates that were determined during the second sub-period when the activity level of the patient satisfies the patient inactivity threshold.

5. The system of claim 3, wherein the second subset of resting heart rates are heart rates of the plurality of heart rates that were determined during the second sub-period when the patient is lying down and the activity level of the patient satisfies the inactivity threshold and.

6. The system of claim 5, wherein the processing circuitry is configured to determine that the patient was at least one of upright or active for a threshold amount of time during the second sub-period based on one or more physiological signals of the patient, and wherein the second subset of resting heart rates are heart rates of the plurality of heart rates that were determined during the second sub-period after the patient was the at least one of upright or active for the threshold amount of time.

7. The system of claim 3, wherein the intervals comprise approximately one minute.

8. The system of claim 1, wherein the representative resting heart rate comprises a minimum value of the second subset of the plurality of heart rates identified as resting heart rates.

9. The system of claim 1, wherein the representative nighttime heart rate comprises a minimum value of the first subset of the plurality of heart rates identified as nighttime heart rates.

10. The system of claim 1, wherein the nocturnal dip comprises a value by which the representative nighttime heart rate differs from the representative resting heart rate.

11. The system of claim 1, wherein the processing circuitry is further configured to generate an alert based on:
comparing the representative resting heart rate to the respective threshold value, wherein the respective threshold value comprises a predetermined number of beats per minute; and
determining that the representative resting heart rate is at least one of equal to or greater than the predetermined number of beats per minute.

12. The system of claim 1, wherein the processing circuitry is further configured to generate an alert based on:
comparing the representative resting heart rate to the respective threshold value, wherein the respective threshold value is based on at least one of a mean or median of the representative resting heart rate determined for one or more previous periods; and
determining that the representative resting heart rate is at least one of equal to or greater than the respective threshold value.

13. The system of claim 1, wherein the processing circuitry is further configured to generate an alert based on:
comparing the nocturnal dip to the respective threshold value, wherein the respective threshold for the nocturnal dip is based on values of nocturnal dip determined for one or more previous periods; and
determining that the nocturnal dip is at least one of equal to or less than the respective threshold value.

14. The system of claim 1, wherein the processing circuitry is further configured to generate an alert based on:
determining whether the nocturnal dip was equal to or less than a predetermined percentage value during one or more previous periods; and
determining that the number of times that the nocturnal dip was equal to or less than the respective threshold value during the one or more previous periods is at least one of equal to or greater than the predetermined number of times.

15. The system of claim 14, wherein the threshold value comprises a predetermined percentage value by which the representative nighttime heart rate differs from the representative resting heart rate.

16. The system of claim 1, further comprising an implantable medical device, wherein the implantable medical device comprises a housing configured for implantation in the patient, wherein the housing includes the sensing circuitry and the processing circuitry.

17. The system of claim 16, wherein the housing of the implantable medical device further includes a plurality of electrodes coupled to the sensing circuitry, and wherein the sensing circuitry is configured to generate a subcutaneous cardiac electrogram based on cardiac signals sensed via the electrodes.

18. A method comprising:
generating, by sensing circuitry configured to sense a cardiac electrogram signal of a patient via a plurality of electrodes, a signal that varies as a function of movement and posture of the patient; and
for each of a plurality of periods, by processing circuitry:
determining a plurality of heart rates of the patient based on the cardiac electrogram signal;
identifying a first subset of the plurality of heart rates as nighttime heart rates wherein each of the first subset of the plurality of heart rates occur when the patient is expected or determined to be asleep;
identifying a second subset of the plurality of heart rates as resting heart rates, wherein each of the second subset of the plurality of heart rates occur when the patient is expected or determined to be awake and when at least one of the patient is lying down or an activity level of the patient satisfies a patient inactivity threshold;
determining a representative nighttime heart rate based on the first subset of the plurality of heart rates;
determining a representative resting heart rate based on the second subset of the plurality of heart rates;
determining a nocturnal dip based on the representative nighttime heart rate and the representative resting heart rate;
comparing at least one of the representative nighttime heart rate, the representative resting heart rate, and the nocturnal dip to a respective threshold value; and
determining whether to generate an alert indicating a change in the cardiac function of the patient based on the comparison.

19. The method of claim 18, wherein each of the plurality of periods comprises approximately one day.

20. The method of claim 18, wherein the plurality of heart rates comprise heart rates determined, by the processing circuitry, at predetermined intervals during a plurality of sub periods, wherein the plurality of sub-periods comprises:
a first sub-period, wherein the first subset of nighttime heart rates are heart rates determined during the first sub-period; and
a second sub-period, wherein the second subset of resting heart rates are heart rates determined during the second sub-period.

* * * * *